(12) United States Patent
Yamane

(10) Patent No.: US 8,403,834 B2
(45) Date of Patent: Mar. 26, 2013

(54) AUTOMATIC RETURN SYRINGE WITH VENTILATION PATHS FOR AIR AND SUCTION PORTS

(75) Inventor: Kenji Yamane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 831 days.

(21) Appl. No.: 12/543,317

(22) Filed: Aug. 18, 2009

(65) Prior Publication Data

US 2010/0048991 A1 Feb. 25, 2010

(30) Foreign Application Priority Data

Aug. 22, 2008 (JP) ................. 2008-213919
Aug. 22, 2008 (JP) ................. 2008-213920

(51) Int. Cl.
*A61B 1/12* (2006.01)
*A61M 5/00* (2006.01)
*A61M 5/30* (2006.01)
*A61M 5/20* (2006.01)

(52) U.S. Cl. .......... 600/159; 600/432; 600/158; 604/68; 604/135

(58) Field of Classification Search .................. 600/159, 600/568, 158, 432, 576, 156, 106; 604/68, 604/522, 189, 197, 135, 240
See application file for complete search history.

(56) References Cited

U.S. PATENT DOCUMENTS

| | | | | |
|---|---|---|---|---|
| 3,016,896 A | * | 1/1962 | Van Sickle | 604/89 |
| 3,143,109 A | * | 8/1964 | Gewertz | 600/579 |
| 3,885,438 A | * | 5/1975 | Harris et al. | 73/863.81 |
| 4,549,554 A | * | 10/1985 | Markham | 600/566 |
| 4,572,210 A | * | 2/1986 | McKinnon | 600/578 |
| 4,664,128 A | * | 5/1987 | Lee | 600/566 |
| 4,667,691 A | * | 5/1987 | Sasa | 134/169 C |
| 4,710,179 A | * | 12/1987 | Haber et al. | 604/211 |
| 5,049,135 A | * | 9/1991 | Davis | 604/181 |
| 5,085,638 A | * | 2/1992 | Farbstein et al. | 604/110 |
| 5,186,839 A | * | 2/1993 | Kimura et al. | 210/656 |
| 5,266,193 A | * | 11/1993 | Kimura et al. | 210/198.2 |
| 5,413,115 A | * | 5/1995 | Baldwin | 600/576 |
| 5,667,500 A | * | 9/1997 | Palmer et al. | 604/533 |

(Continued)

FOREIGN PATENT DOCUMENTS

| | | | |
|---|---|---|---|
| JP | 57-103621 A | 6/1982 | |
| JP | 6-070880 A | 3/1994 | |

(Continued)

*Primary Examiner* — John P Leubecker
*Assistant Examiner* — Ronald D Colque
(74) *Attorney, Agent, or Firm* — Birch, Stewart, Kolasch & Birch, LLP

(57) ABSTRACT

The inside of a cylindrical body is divided into two parts, that is, a first and a second chamber, and in a piston body, a first ventilation hole and a first ventilation path of a pushing portion are formed so as to communicate with the first chamber and a second ventilation hole and a second ventilation path of the pushing portion are formed to communicate with the second chamber, and a spring for returning the piston body to its original position is provided. By pressing the pushing portion while closing the first ventilation port so as to advance the piston body, air is supplied through a syringe port on the first chamber, while by pressing the pushing portion while closing the second ventilation port, air is supplied through the syringe port on the second chamber, and by releasing the pushing operation, the piston body automatically returns to the original position.

4 Claims, 21 Drawing Sheets

U.S. PATENT DOCUMENTS

| | | | |
|---|---|---|---|
| 5,827,941 A * | 10/1998 | Good et al. | 73/1.19 |
| 6,584,910 B1 * | 7/2003 | Plass | 102/512 |
| 7,691,087 B2 * | 4/2010 | Gough et al. | 604/165.01 |
| 7,935,078 B2 * | 5/2011 | Horita et al. | 604/82 |
| 2002/0165501 A1 * | 11/2002 | Yang | 604/240 |
| 2003/0199816 A1 * | 10/2003 | Ramming | 604/89 |
| 2004/0116870 A1 * | 6/2004 | Thomas | 604/182 |
| 2005/0202365 A1 * | 9/2005 | Cao et al. | 433/89 |
| 2008/0103367 A1 * | 5/2008 | Burba et al. | 600/236 |
| 2009/0209821 A1 * | 8/2009 | Yamane | 600/156 |
| 2009/0209823 A1 * | 8/2009 | Yamane | 600/158 |
| 2010/0022974 A1 * | 1/2010 | Sharratt et al. | 604/317 |

FOREIGN PATENT DOCUMENTS

JP    2003-135391 A    5/2003

* cited by examiner

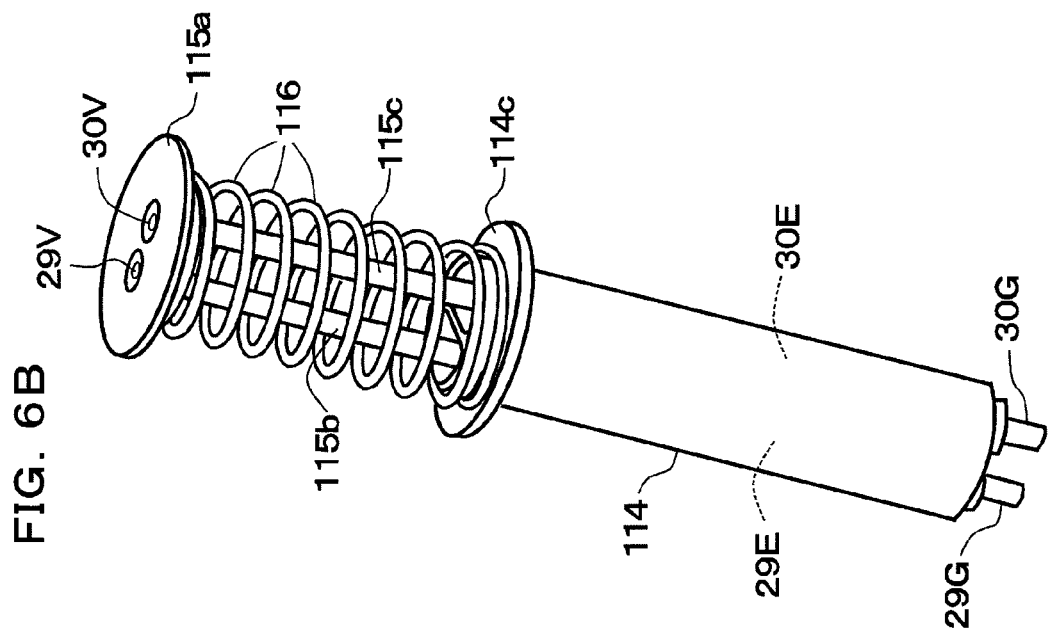
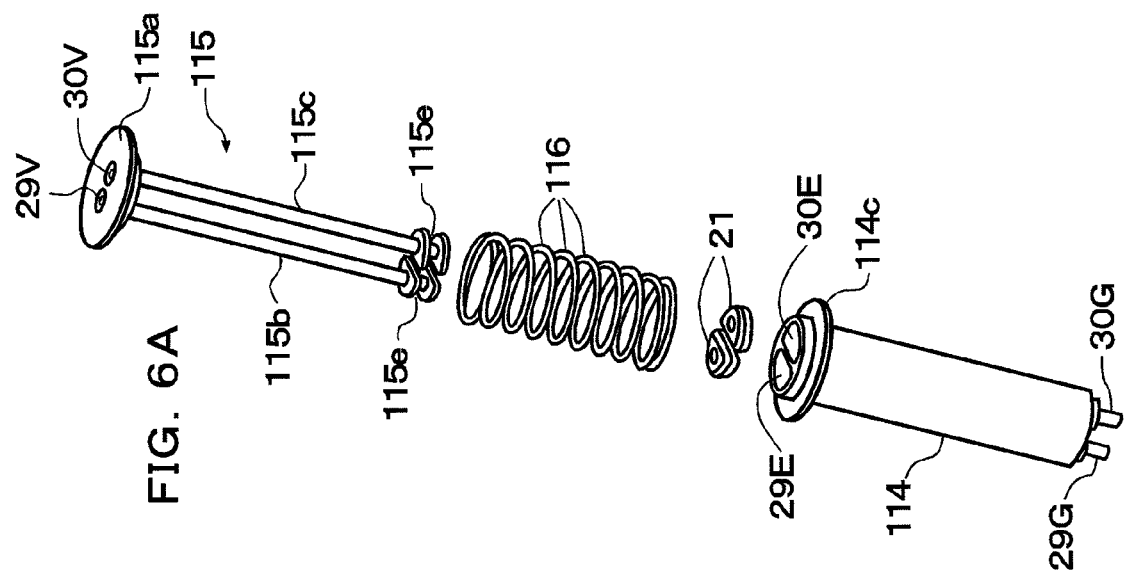

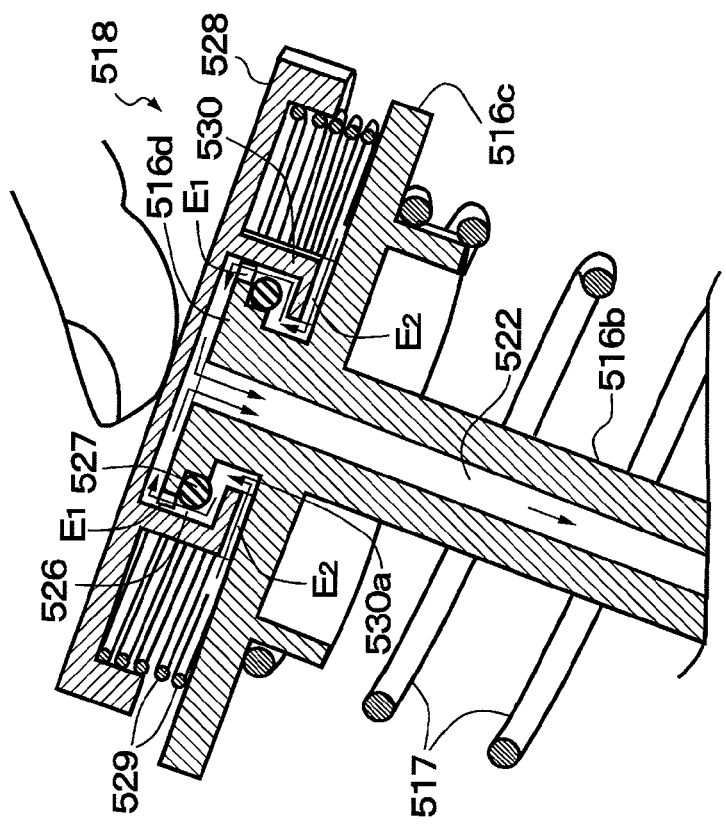
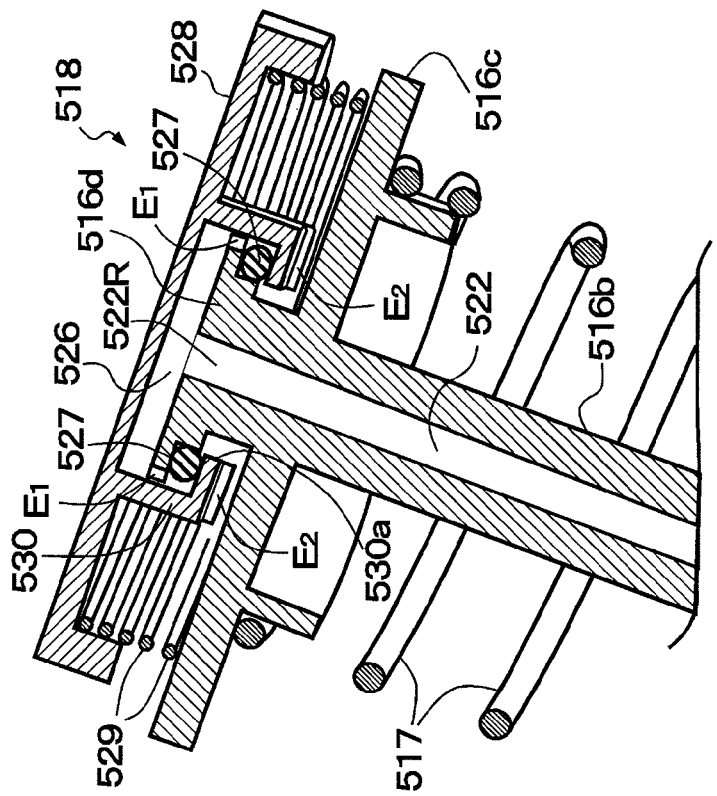

AUTOMATIC RETURN SYRINGE WITH VENTILATION PATHS FOR AIR AND SUCTION PORTS

BACKGROUND OF THE INVENTION

The disclosure of Japanese Patent Applications Nos. 2008-213919 and 2008-213920 filed on Aug. 22, 2008, including its specification, claims and drawings, is incorporated herein by reference in its entirety.

1. Field of the Invention

The present invention relates to an automatic return syringe and, more particularly to a configuration of a syringe used for air/water supply using an air/water supply tube disposed in an endoscope or the like and for suctioning through a suction tube and portable as an air/water supply device or suctioning device.

2. Description of the Related Art

FIG. 22 shows a configuration of a prior-art endoscope device, and an endoscope has a distal end portion 1A provided with a solid-state image pickup device, an operation portion 1B provided through a bent portion and the like, for example. In this endoscope, an air/water supply tube 3a and a water supply tube 3b and an air supply tube 3c branching from the air/water supply tube 3a are disposed for washing an observation window arranged on a distal end face, a treatment instrument insertion channel 5a and a suction tube 5b connected to the treatment instrument insertion channel 5a are disposed from a forceps port 4 through which the treatment instrument is to be introduced to the distal end face of the distal end portion 1A, and the treatment instrument insertion channel 5a also functions as a suction tube.

On the operation portion 1B, an air/water supply button 6a for switching between the water supply tube 3b and the air supply tube 3c and for operating air/water supply, a suction button 6b, a camera shutter button 6c and the like are provided. A pump 8 for air/water supply is connected to the water supply tube 3b, through a water supply tank 7 filled with washing water, the pump 8 for air/water supply is directly connected to the air supply tube 3c, and a pump 10 for suction is connected to the suction tube 5b through a suction tank 9.

FIG. 23 shows a configuration of an air/water supply operation portion having the air/water supply button 6a, and in the air/water supply operation portion, a shaft portion (pusher portion and a piston) 11 is arranged inside a receiving portion 10 capable of vertical movement through a spring, and an upper part of the shaft portion 11 becomes the air/water supply button 6a. The water supply tube 3b and the air supply tube 3c are installed in the receiving portion 10, and an air supply path 12E, an outside air opening path 12F, and a water supply path 13E are formed in the shaft portion 11.

According to the endoscope device as above, air fed by an operation of the pump 8 flows into outside air from the air supply tube 3c through the outside air opening path 12F, and when the upper face of the air/water supply button 6a (shaft portion 11) is pressed and the outside air opening path 12F is blocked (air supply operation), the air supply path 12E communicates with the air supply tube 3c so that the air supply from the pump 8 is carried out from a nozzle on the distal end face to the observation window. On the other hand, by pressing the air/water supply button 6a (water supply operation), the air supply tube 3c is closed, and the water supply path 13E communicates with the water supply tube 3b so that the washing water in the water supply tank 7 is injected toward the observation window. By means of the above air supply and water supply, stains or the like adhering on the observation window is removed, and an observation state of an observed body can be maintained favorably.

Alternatively, by operating the suction button 6a, a liquid of the observed body (contents) or the like is sucked through the treatment instrument insertion channel 5a and the suction tube 5b by a suctioning operation of the pump 10 for suction so that the liquid or the like can be discharged to the suction tank 9. The above explanation was made on an example of a mechanical valve, but the air/water supply, suction can be carried out using an electric button (switch) and an opening/closing valve.

However, if the air/water supply, suction are carried out with the prior-art endoscope device, the pump 8 for air/water supply (device) and the pump 10 for suction are needed as mentioned above, and there is a problem of a difficulty in use of the endoscope at facilities where the pump 8 for air/water supply or the pump 10 for suction is not arranged.

Portability of the endoscope device has enabled use thereof at various places other than fully-equipped facilities, use at the bedside, use in emergency and the like, and simplification of the configuration leads to cost reduction. Thus, if devices relating to air supply, water supply or suction can be made portable and simplified, a highly convenient endoscope device can be provided.

Also, a syringe used in general can perform any one of air supply, water supply or suction once by pushing and operating the piston manually but cannot perform continuous air supply, water supply or suction without limitation on supply amount.

The present invention was made in view of the above problems and has an object to provide an automatic return syringe that can perform continuous air supply, water supply or suction easily without limitation on supply amounts and is capable of portability and simplification of devices relating to air supply, water supply or suction leading to portability and simplification of an endoscope device.

SUMMARY OF THE INVENTION

In order to achieve the above object, the automatic return syringe according to the present invention comprises a cylindrical body in which a plurality of space portions divided by a partition portion are formed with a syringe port (an air supply port) provided at each of the plurality of space portions, a piston body, which is a piston reciprocally moving in the plurality of space portions in the cylindrical body and having a pusher portion at a rear end, in which a plurality of ventilation paths through which each of the plurality of space portions communicates with each of a plurality of ventilation holes provided in the pusher portion, and a spring arranged between the piston body and the cylindrical body, for returning the piston body subjected to the pushing operation to an original position.

In the invention, the plurality of space portions may be installed in series by laterally dividing the inside of the cylindrical body, and in the space portion other than a distal-end space portion, the syringe port is provided on a side face of the cylindrical body, and the piston body may have a piston portion reciprocally moving in close contact with an inner periphery of the plurality of space portions of the cylindrical body and a shaft portion supporting the piston portion and having an outer diameter smaller than an inner diameter of the cylindrical body.

Alternatively, the plurality of space portions may have parallel arrangement by longitudinally dividing the inside of the cylindrical body, and the syringe port may be provided on the distal end side of the cylindrical body.

Moreover, the syringe port for air supply may be arranged on the distal end side of the plurality of space portions arranged in series or in parallel in the cylindrical body, and a suction port may be provided on a side face of the cylindrical body on a rear side from a position of the piston portion arranged in the plurality of space portions when the piston portion is not operated so that both air supply and suction can be performed.

According to the configuration of the present invention, the plurality of syringe space portions (space portions in which the piston reciprocally moves)independent from each other are formed in series or in parallel in the cylindrical body, and by pressing the pusher portion while closing one (or two or the like) of the plurality of ventilation holes with the thumb or the like so as to advance the piston body, air in the applicable space portion is pushed out of the respective syringe port, and by releasing the thumb after that, the air flows into the applicable space portion through the ventilation hole and the ventilation path of the pusher portion, the piston body is automatically returned (retreated) by the spring to the original position. Therefore, the operator can perform continuous air supply using the space portion selected from the plural by repeating the action of pressing and releasing the pusher portion.

According to the automatic return syringe of the present invention, by repeating the pressing operation, continuous air/water supply or suction can be performed by a single syringe easily without limitation on a supply amount. That is, if air/water supply or suction is to be performed in an endoscope device, for example, a syringe needs to be mounted on each of the air supply tube, the water supply tube or the suction tube, and if a single syringe is to be used, the syringe needs to be re-connected to each of the tubes. In the former case, a connection configuration of the plurality of syringes becomes complicated, while in the latter case, a connection operation becomes cumbersome. With the invention of the present application, by connecting the respective syringe ports to the air supply tube, the water supply tube or the suction tube, a plurality of operations of air supply, water supply or suction can be performed with a single syringe.

In the case of the endoscope device, by forming a first space portion having a first syringe port and a second space portion having a second syringe port on the cylindrical body, by providing first and second ventilation holes and first and second ventilation paths in the piston body, by connecting an endoscope air supply tube to the first syringe port by a connection tube or the like, and by connecting a water supply tank connected to an endoscope water supply tube to the second syringe port, for example, air supply can be preformed from the first syringe port through the endoscope air supply tube, and water such as washing water or the like can be supplied from the second syringe port through the water supply tank and the endoscope water supply tube.

Also, if the one having a suction port arranged is applied to the endoscope device, in addition to connection of the above-mentioned two syringe ports to the endoscope for air/water supply, by connecting the suction tank to which an endoscope suction tube is connected using the connection tube or the like to the suction port provided on the side face of the cylindrical body, a liquid or the like in the observed body can be suctioned through the treatment instrument insertion channel and the suction tube in the endoscope by means of sucked air from this suction port.

By applying the present invention to the endoscope device as above, such advantages can be obtained that improved portability and simplification of devices relating to air/water supply or further improved portability and simplification of the endoscope device can be realized, use of an endoscope at various places other than fully-equipped facilities, bedside, emergency and the like is facilitated, and highly convenient endoscope device can be obtained.

Also, the automatic return syringe according to another invention has a cylindrical body having a syringe port formed on a side face, a piston body reciprocally moving in close contact with an inner face of the cylindrical body and having a first ventilation path formed in order to flow the outside air into the cylindrical body, a first urging member arranged between the piston body and the cylindrical body and retreating the advanced piston body to its original position, and a pusher body connected so as to reciprocally move with respect to the piston body and to become a pusher portion of the piston body, comprises a pushing operation portion which is brought to an open state when the pusher body is advanced and to a closed state when the pusher body is retreated and having a second ventilation path formed communicating with the first ventilation path in order to flow the outside air into the cylindrical body in the open state and a second urging member arranged between the pusher body of the pushing operation portion and the piston body, for retreating the pusher body which has been advanced by the pushing operation to the original position, in which when the pusher body of the pushing operation portion is pressed, the piston body is advanced while the outside air is made to flow into the cylindrical body through the open-state second ventilation path and first ventilation path, and when the pushing operation of the pusher body is released, the second ventilation path is brought into the closed state, and air supply from the syringe port is performed while the piston body is retreated by the first urging member to the original position.

According to the configuration of this another invention, by pressing the pusher body of the pushing operation portion with the thumb or the like against the second urging member so as to advance the pusher body (first-stage pressing operation), the second ventilation path in the pushing operation portion is brought into the closed state, and then, by pressing the piston body by the pusher body against the first urging member (second-stage pressing operation), the piston body is advanced and moved to the distal end side while the outside air flows into the cylindrical body through the first ventilation path and the second ventilation path. After that, by releasing the pressing operation, the pusher body is retreated by the second urging member, the second ventilation path in the pushing operation portion is brought into the closed state, and air inflow from the first ventilation path and the second ventilation path is stopped, but at the same time, the piston body is retreated by the first urging member, and as a result, air supply from the syringe port is performed by the air in the cylindrical body. The piston body automatically returns to the original position by the first urging member, and by the repeated operation of the pushing operation portion, continuous air supply is made possible regardless of the capacity in the cylindrical body.

Also, by using the automatic return syringe of this another invention as the air/water supply device for the endoscope device, the syringe port of the cylindrical body can be tube-connected to an air supply port of the endoscope or to the water supply tank tube-connected to a water supply port of the endoscope. In this case, by connecting the syringe port to the air supply port of the endoscope by piping, air supply to the observation window, for example, can be performed through the air supply tube of the endoscope, and by connecting the syringe port to the water supply tank, water in the water supply tank can be supplied from the water supply port of the endoscope to the water supply tube so as to perform the water supply to the observation window.

Moreover, in this endoscope device, an air/water supply operation portion comprising a cylindrical receiving portion in which an air supply tube and a water supply tube are disposed, a first shaft body arranged in the receiving portion capable of vertical movement and having a connection path communicating with the air supply tube of the receiving portion formed when it is pressed down by a first-stage pusher portion (air supply pusher portion), and a second shaft body arranged on an outer periphery side of the first shaft body capable of vertical movement and having a connection path communicating with the water supply tube of the receiving portion formed when it is pressed down by a second-stage pusher portion (water supply pusher portion) is provided so that air/water supply can be performed using the automatic return syringe by operations of the first-stage pusher portion and the second-stage pusher portion of the air/water supply operation portion.

In this case, after the syringe portion is connected to the air supply port or water supply port, by keeping the piston body pressed, an air supply force is kept charged for air/water supply, and air supply of an amount according to necessity can be performed appropriately and easily by the operation of the first-stage pusher portion of the first shaft body in the air/water supply operation portion, and also, water supply of an amount according to necessity can be performed appropriately and easily by the operation of the second-stage pusher portion of the second shaft body.

With the automatic return syringe of the another invention, too, by repeating the pressing operation in two stages by the pusher body, such an advantage can be obtained that continuous air supply or water supply can be performed easily without limitation on the supply amount. Also, according to the endoscope device using the automatic return syringe, advantages such as improved portability, simplification of the devices relating to air/water supply and further improved portability and simplification of the endoscope devices, facilitated use of the endoscope at various places other than fully-equipped facilities, bedside, emergency and the like, and highly convenient endoscope devices can be obtained.

BRIEF DESCRIPTION OF THE DRAWINGS

FIG. 6A is an exploded perspective view of the syringe of the second embodiment;

FIG. 6B is a perspective view of the syringe of the second embodiment when the syringe is not operated;

FIGS. 17A to 17D show a configuration of a pushing operation portion of the automatic return syringe of the fifth embodiment, in which FIG. 17A is a diagram of a small disc portion seen from a rear end side, FIG. 17B is a longitudinal sectional view of the small disc portion of the pushing operation portion, FIG. 17C is a longitudinal sectional view of a surrounding body of the pushing operation portion, and FIG. 17D is a diagram of the surrounding body of the pushing operation portion seen from a distal end side;

FIG. 18A is a sectional view of the pushing operation portion of the automatic return syringe of the fifth embodiment in an enlarged manner when the syringe is not operated;

FIG. 18B is a sectional view in the pushing operation;

DETAILED DESCRIPTION OF THE PREFERRED EMBODIMENTS

First Embodiment

Figure 1:
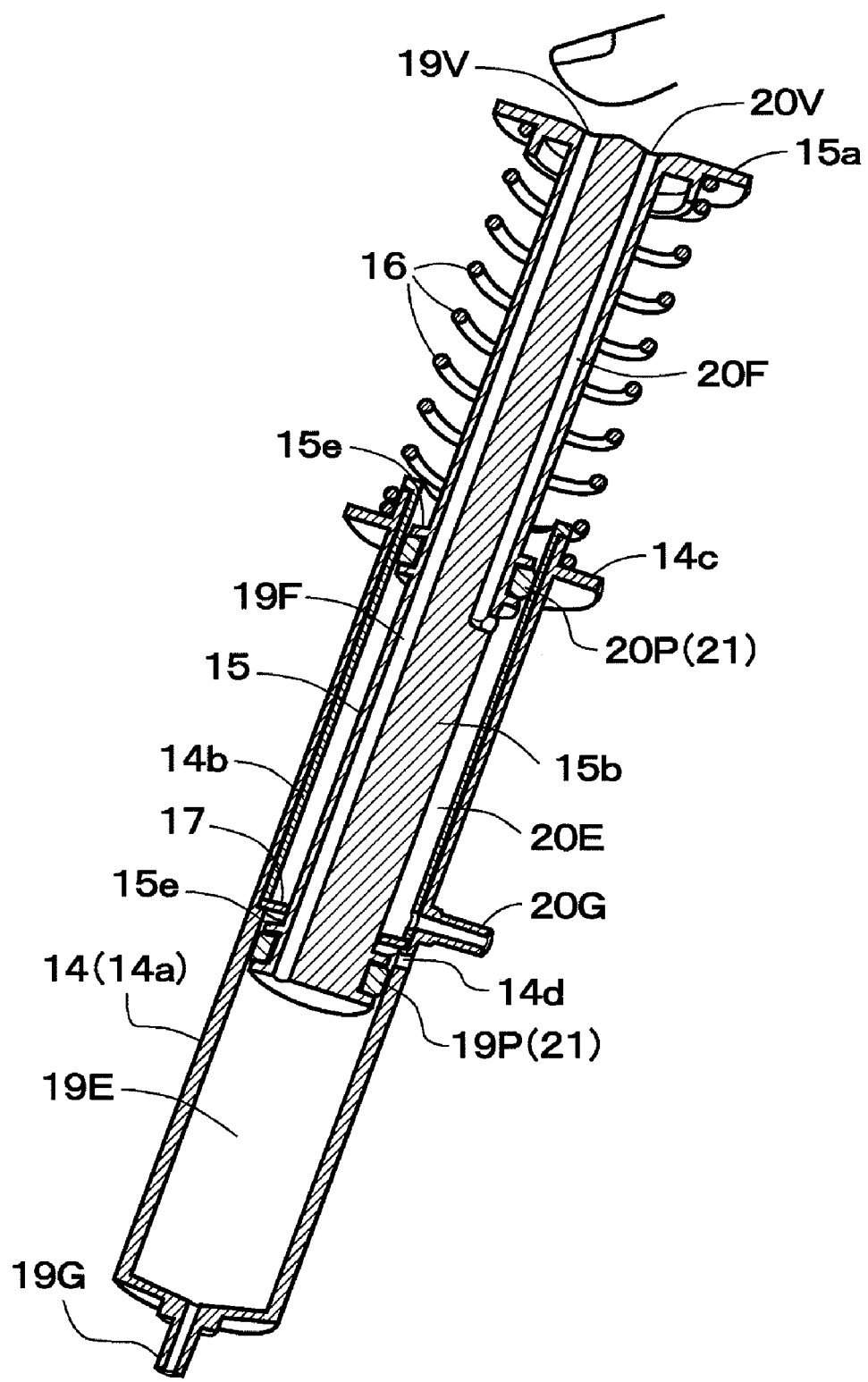
FIG. 1 is a sectional view illustrating a configuration of an automatic return syringe according to a first embodiment of the present invention.
Figure 2:
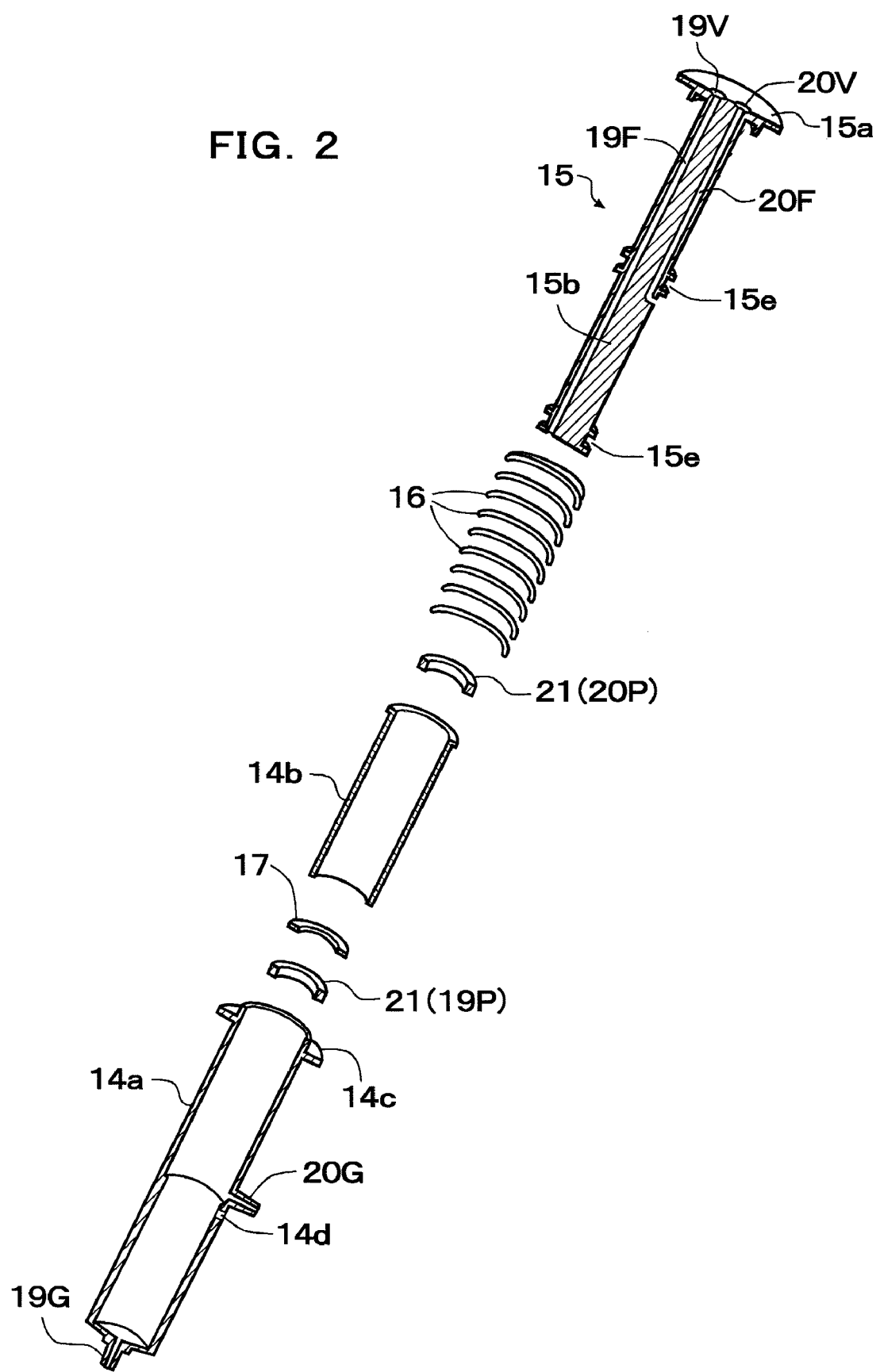
FIG. 2 is an exploded perspective view of the syringe in the first embodiment in a cut-off state.

FIGS. 1 to 4 show a configuration of an automatic return syringe according to a first embodiment, and in this first embodiment, two syringe space portions are arranged in series. As shown in FIG. 1, a syringe in the embodiment comprises a cylindrically-shaped cylindrical body 14, a piston body (slider) 15, and a spring 16, and in the cylindrical body 14, a short second cylindrical body 14b is mounted on a first cylindrical body 14a so as to be abutted into a step of an internal intermediate portion, and a partition plate 17 is arranged at a distal end (stepped portion) of the second cylindrical body 14b so that a first chamber (front chamber) 19E and a second chamber (rear chamber) 20E are formed in the cylindrical body 14 as syringe space portions through which a piston portion reciprocally moves. A first syringe port (air supply port) 19G is provided a distal end of the first chamber 19E (cylindrical body 14), a second syringe port 20G is provided on a side face of the cylindrical body 14 on the distal end side of the second chamber 20E, and a ventilation port 14d is formed on the side face of the cylindrical body 14 below the partition plate 17 on the rear end side of the first chamber 19E.

On the other hand, the piston body 15 is provided with a disc-shaped pusher portion 15a arranged at a rear end thereof for performing a piston operation by being pushed with the thumb or the like and a columnar-rod shaped shaft portion 15b having an outer diameter smaller than an inner diameter of the cylindrical body 14 and is also provided with a first piston portion (sliding portion) 19P at the distal end, sliding (reciprocally moving) in close contact with an inner face of the cylindrical body 14, and a similar second piston portion 20P in an intermediate portion. The first and second piston portions 19P, 20P are formed by mounting a ring-like rubber (elastic rubber) member 21 for close contact with the inner face of the cylindrical body on a fitting portion (annular groove portion, for example) 15e of the columnar-rod shaped shaft portion 15b.

Also, in the piston body 15, a first ventilation hole 19V and a second ventilation hole 20V are formed in the pusher portion 15a, and a first ventilation path (conduit) 19F penetrating from the first ventilation hole 19V to the shaft-portion distal end in the axial direction and a second ventilation path 20F penetrating from the second ventilation hole 20V to the side face in the middle of the shaft portion are provided in the shaft portion 15b. Moreover, the spring 16 for urging the pushed piston body 15 to a direction to return to the original position is provided between a flange portion 14c on the rear side of the cylindrical body 14 and the pusher portion 15a of the piston body 15 (in a fitted state with each of them).

Figure 3:
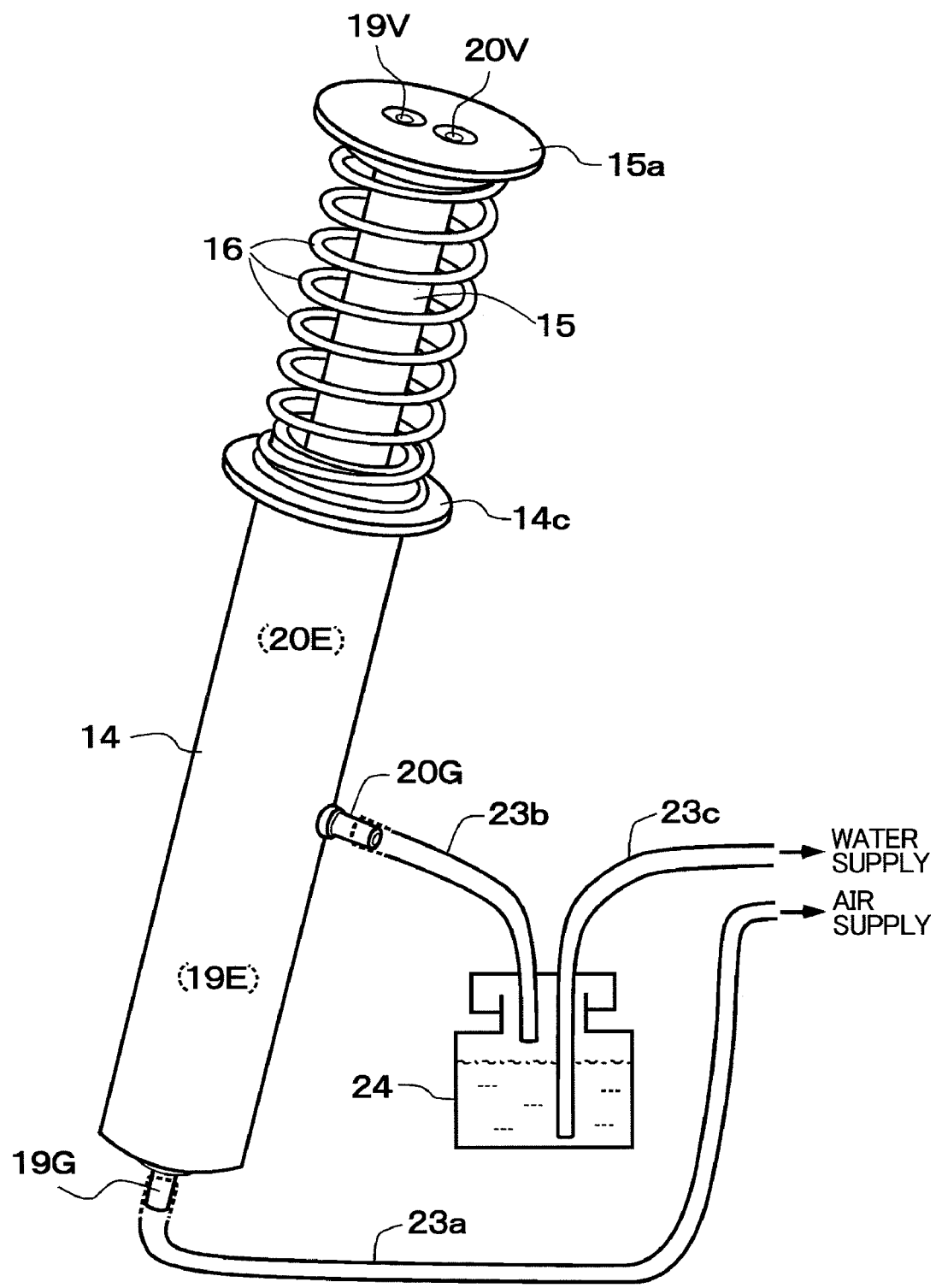
FIG. 3 is a diagram illustrating a configuration when the syringe of the first embodiment is applied to an endoscope.
Figure 4:
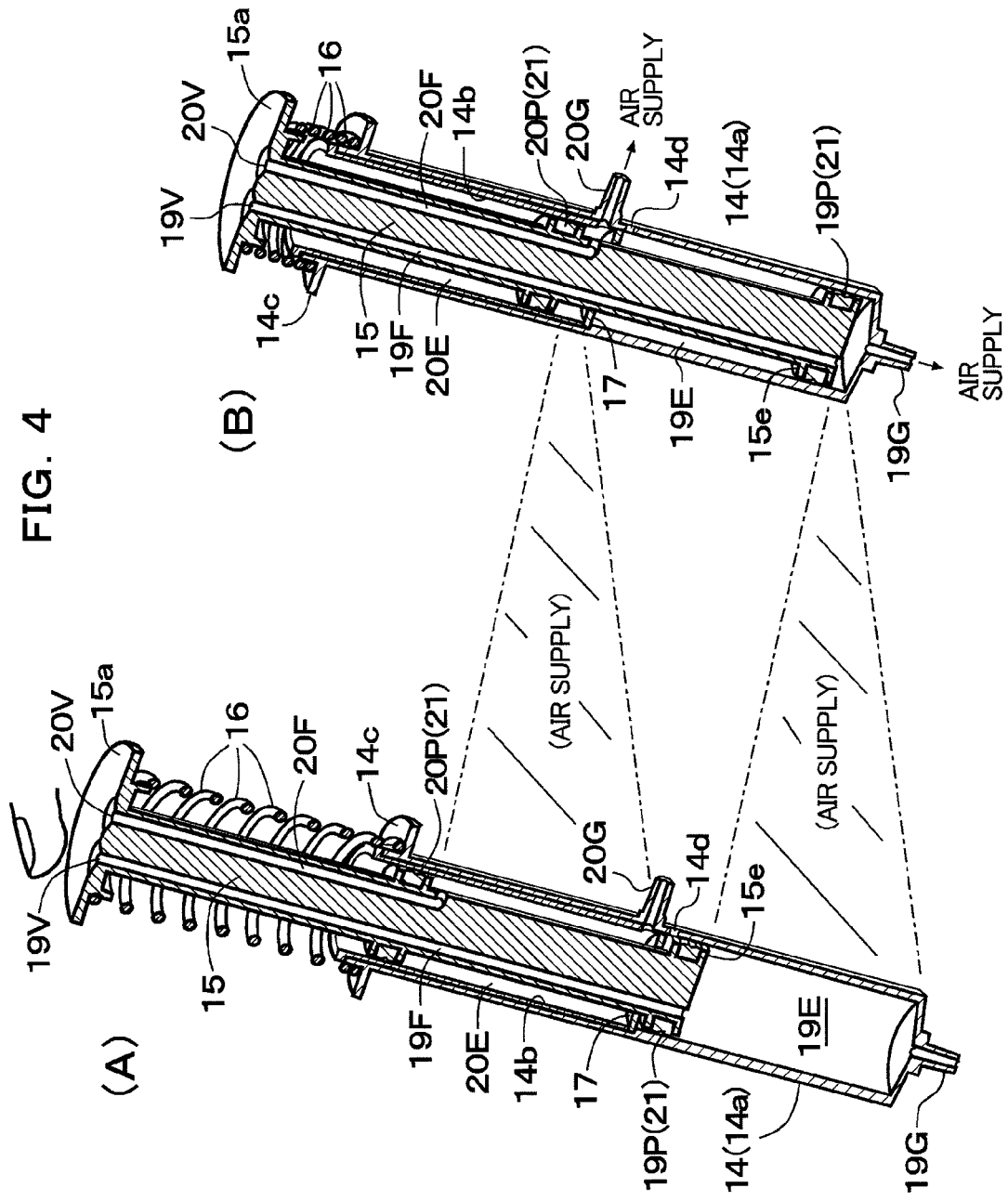
FIG. 4 show an operation of the syringe of the first embodiment, in which (A) is a sectional view when the syringe is not operated, while (B) is a sectional view when the syringe is subjected to a pushing operation.

FIG. 3 shows a configuration in which the syringe of the first embodiment is applied to an endoscope device and air/water supply is performed, and in this case, an air supply tube of the endoscope is connected to the first syringe port 19G of the first chamber 19E in the cylindrical body 14 through a connection tube 23a, and a water supply tank 24 storing washing water or the like is mounted on the second syringe port 20G of the second chamber 20E through a connection tube 23b, and the water supply tank 24 is connected to a water supply tube of the endoscope through a connection tube 23c.

According to the syringe of the first embodiment as the above, by pressing the pusher portion 15a with the thumb or the like (against an urging force of the spring 16) while closing the first ventilation hole 19V, from a basic state (non-operated period) in FIG. 4A, air is sucked through the ventilation port 14d and air in the first chamber 19E (cylindrical body 14) is pushed out through the first syringe port 19G so that air can be supplied, and by pressing the pusher portion 15a while closing the second ventilation hole 20V, air in the second chamber 20E is pushed out through the second syringe port 20G and air can be supplied. On the other hand, if the pressing operation on the pusher portion 15a is released from a state in FIG. 4B, the first ventilation hole 19V and the second ventilation hole 20V are opened, and the piston body 15 is urged by the spring 16 to the rear side, and thus, outside air is supplied from the first ventilation hole 19V and the second ventilation hole 20V through the first ventilation path 19F and the second ventilation path 20F into the first chamber 19E and the second chamber 20E, and the air having flown into the first chamber 19E is discharged through the ventilation port 14d and the piston body 15 is automatically returned to the original state in FIG. 4A. Therefore, by performing the pressing operation on the pusher portion 15a repeatedly, air can be supplied plural times continuously through the selected syringe port 19G or 20G.

If applied to the endoscope as shown in FIG. 3, by pressing the pusher portion 15a while closing the first ventilation hole 19V, air is supplied to the observation window through the air supply tube of the endoscope through the first syringe port 19G, or by pressing the pusher portion 15a while closing the second ventilation hole 20V, air is supplied through the second syringe port 20G and water is supplied to the observation window through the water supply tube of the endoscope via the water supply tank 24. As mentioned above, by means of the continuous operation on the pusher portion 15a, air/water supply without limitation on the supply amount is realized.

Second Embodiment

Figure 5:
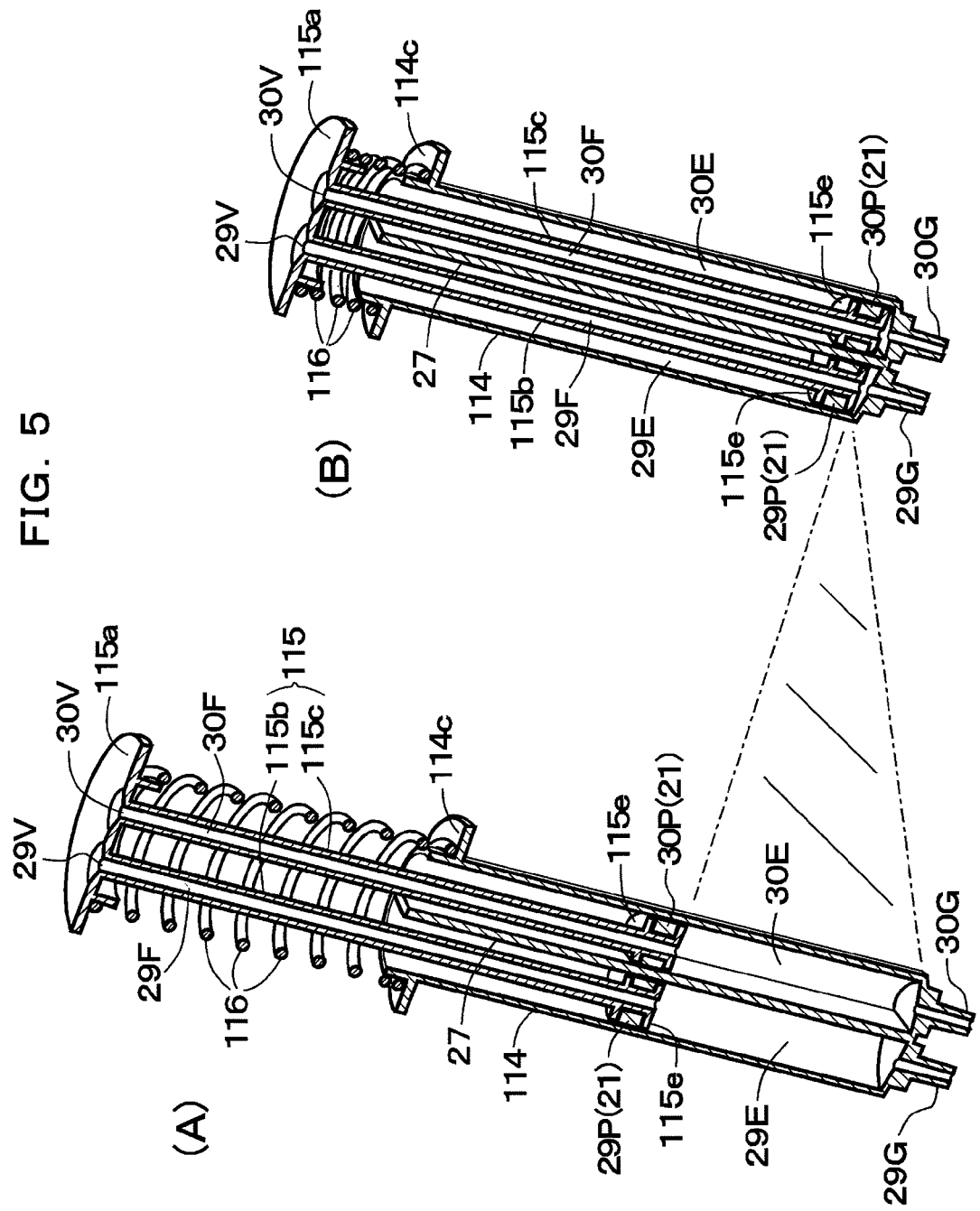
FIG. 5 show a configuration of an automatic return syringe according to a second embodiment, in which (A) is a sectional view in which the syringe is not operated, while (B) is a sectional view when the syringe is subjected to the pushing operation.

FIGS. 5 and 6 show a configuration of a second embodiment in which two syringe space portions are arranged in parallel, and as shown in the figures, the syringe in the second embodiment also comprises a cylindrically-shaped cylindrical body 114, a piston body 115 and a spring 116, and in the cylindrical body 114, by arranging the partition plate 27 so as to divide a columnar space inside longitudinally into two parts, a first chamber 29E and a second chamber 30E as syringe space portions in which the piston portion reciprocally moves are formed in parallel inside. A first syringe port 29G is provided at a distal end of the first chamber 29E (cylindrical body 14), while a second syringe port 30G is provided at a distal end of the second chamber 30E.

On the other hand, the piston body 115 is provided with a disc-shaped pusher portion 115a at its rear end and two columnar-rod shaped shaft portions 115b, 115c, and a first piston portion 29P sliding in close contact with an inner face of the first chamber 29E is provided at a distal end of the shaft portion 115b and a second piston portion 30P sliding in close contact with an inner face of a cylindrical body of the second chamber 30E is provided at a distal end of the shaft portion 115c. The first and second piston portions 29P and 30P are formed by mounting the annular rubber member 21 for close contact with inner face of each chamber on a fitting portion (annular groove portion, for example) 115e of the columnar-rod shaped shaft portions 115b, 115c. The shaft portions 115b, 115c may have a size (diameter) such that its entire outer periphery is brought into close contact with the inner wall of each of the chambers 29E, 30E.

Also, in the piston body 115, a first ventilation hole 29V and a second ventilation hole 30V are formed in the pusher portion 115a, and in the shaft portion 115b, a first ventiltion path 29F penetrating from the first ventilation hole 29V to the distal end of the shaft portion is provided in the axial direction, while in the shaft portion 115c, a second ventilation path 30F penetrating from the second ventilation hole 30V to the distal end of the shaft portion is provided. Moreover, the spring 116 for urging the piston body 115 having advanced to a direction to return to the original position is provided between a flange portion 114c on the rear side of the cylindrical body 114 and the pusher portion 115a.

According to the syringe of the second embodiment as above, by pressing the pusher portion 115a with the thumb or the like (against the urging force of the spring 116) while closing the first ventilation hole 29V from the basic state (non-operated period) in FIG. 5A, air in the first chamber 19E is pushed out through the first syringe port 29G and air can be supplied, while by pressing the pusher portion 115a while closing the second ventilation hole 30V, air in the second chamber 30E is pushed out through the second syringe port 30G and air supply can be performed. On the other hand, if the pressing operation on the pusher portion 115a is released from the state in FIG. 5B, the first ventilation hole 29V and the second ventilation hole 30V are opened, and the piston body 115 is urged by the spring 116 to the rear side so that the outside air is supplied into the first chamber 29E and the second chamber 30E from the first ventilation hole 29V and the second ventilation hole 30V through the first ventilation path 29F and the second ventilation path 30F, and the piston body 115 is automatically returned to the original state in FIG. 5A. As mentioned above, by operating the pusher portion 115a repeatedly, air can be supplied from the selected syringe port 29G or 30G without limitation on the supply amount.

This second embodiment can be also applied to the endoscope device for performing air/water supply, and in this case, it is only necessary that the air supply pipe of the endoscope is connected to the first syringe port 29G, for example, through a connection tube (23a) as in FIG. 3 and the water supply tank 24 is mounted on the second syringe port 30G through the connection tube (23b). According to this, by pressing the pusher portion 115a while closing the first ventilation hole 29V, air is supplied through the first syringe port 29G, or by pressing the pusher portion 115a while closing the second ventilation hole 30V, water is supplied by air supply from the second syringe port 30G.

Third Embodiment

Figure 7:
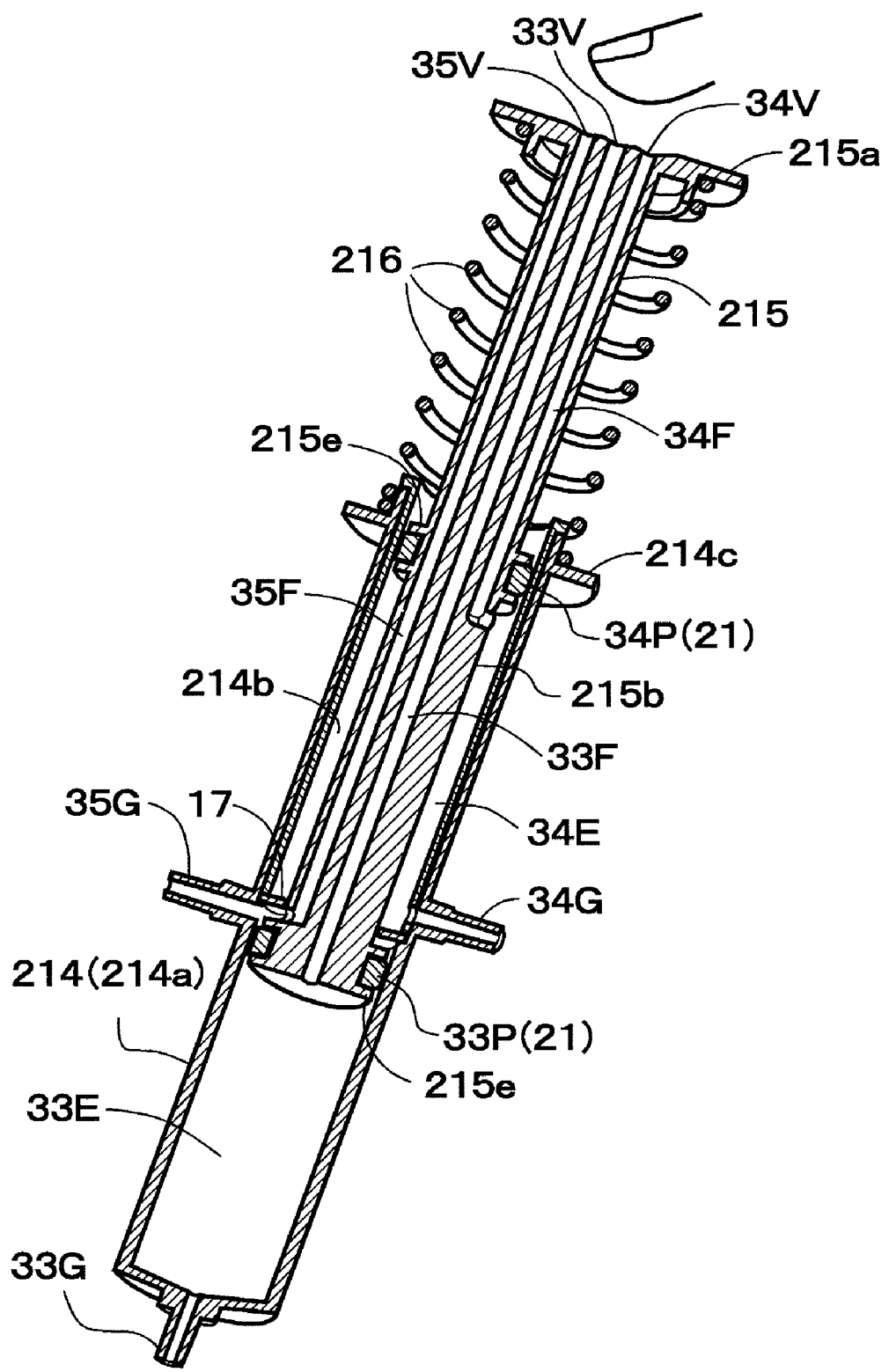
FIG. 7 is a sectional view illustrating a configuration of an automatic return syringe of a third embodiment.
Figure 8:
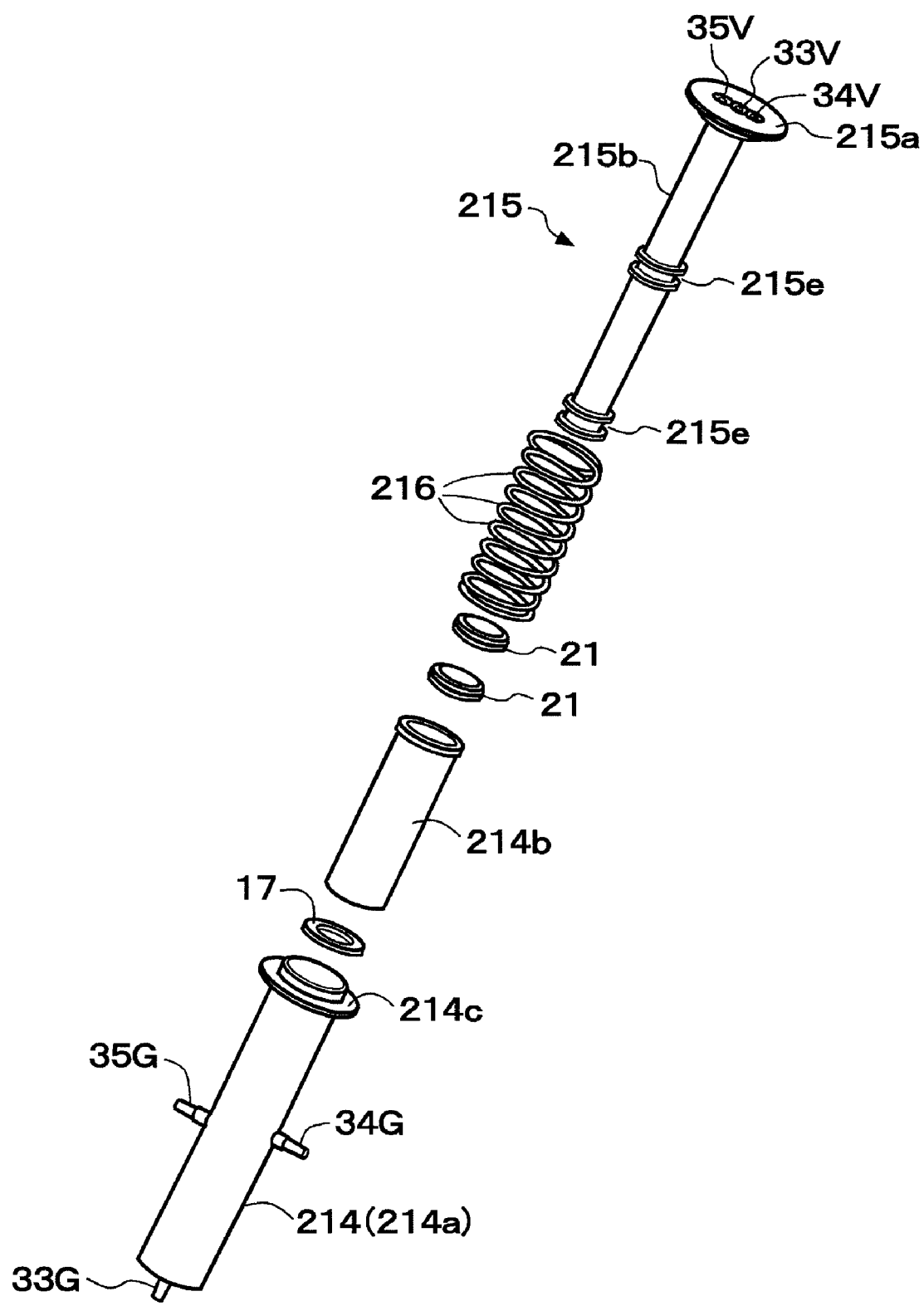
FIG. 8 is an exploded perspective view illustrating a configuration of the syringe of the third embodiment.

FIGS. 7 to 10 show a configuration of a third embodiment, and this third embodiment is a configuration in which two syringe space portions are arranged in series similarly to the first embodiment, in which suctioning can be also performed. As shown in FIG. 7, the syringe in the third embodiment comprises a cylindrically-shaped cylindrical body 214, a piston body 215, and a spring 216, and in the cylindrical body 214, by mounting a second cylindrical body 214b so that it is abutted against a step of an inner intermediate portion of a first cylindrical body 214a and by arranging the partition plate 17 at a distal end (stepped portion) of the second cylindrical body 214b, a first chamber 33E and a second chamber 34E as syringe space portions through which a piston portion reciprocally moves are formed in the cylindrical body 214. A first syringe port 33G is provided at a distal end of the first chamber 33E (cylindrical body 214) and a second syringe port 34G is provided on a side face of the cylindrical body 214 on the distal end side of the second chamber 34E.

On the other hand, the piston body 215 is provided with a disc-shaped pusher portion 215a at its rear end and a columnar-rod shaped shaft portion 115b having an outer diameter smaller than an inner diameter of the cylindrical body 214 and is also provided with a first piston portion (sliding portion) 33P reciprocally moving in close contact with an inner face of the cylindrical body 214 at a distal end and a second piston portion 34P similarly at an intermediate portion. The first and second piston portions 33P and 34P are formed by mounting the annular rubber member 21 for close contact with the inner face of the cylindrical body to a fitting portion (annular groove portion, for example) 215e of the columnar-rod shaped shaft portion 215b.

Also, in the piston body 215, a first ventilation hole 33V and a second ventilation hole 34V are formed in the pusher portion 215a, and a first ventilation path 34F penetrating from the first ventilation hole 33V to the shaft portion distal end in the axial direction and a second ventilation path 34F penetrating from the second ventilation hole 34V to the side face of the middle of the shaft portion are provided in the shaft portion 215b.

In the third embodiment, a configuration for suctioning is added, and a suction port 35G is provided on the side face of the cylindrical body 214 below the partition plate 17 on the rear end side of the first chamber 33E, and the first chamber 33E is also used as a space portion for suctioning. That is, the suction port 35G also functions as a ventilation port (14d in the first embodiment) for the reciprocal motion of the piston body 215 in air supply using the first chamber 33E. In the piston body 215, a third ventilation hole 35V is formed in the pusher portion 215a, and a third ventilation path 35F penetrating from the third ventilation hole 35V to the shaft portion distal end is provided in the shaft portion 215b. The spring 216 is provided between a flange portion 214c on the rear side of the cylindrical body 214 and the pusher portion 215a of the piston body 215 so as to urge the pushed piston body 215 to the direction to return to the original position.

By providing a partition plate (17) on the rear end side of the second chamber 34E, the second chamber 34E is used as a closed space, while by providing the suction port (35G) on the rear end side of the second chamber 34E and by forming the third ventilation hole 35V shorter, the second chamber 34E can be also used as a space portion for suctioning. Alternatively, a fourth ventilation hole and a fourth ventilation path may be provided so that the second chamber 34E is used as a space portion for the second suctioning. The first to third ventilation holes 33V to 35V are arranged in a straight-line state, but they may be arranged in the circumferential direction as three-apex arrangement of a triangle.

Figure 9:
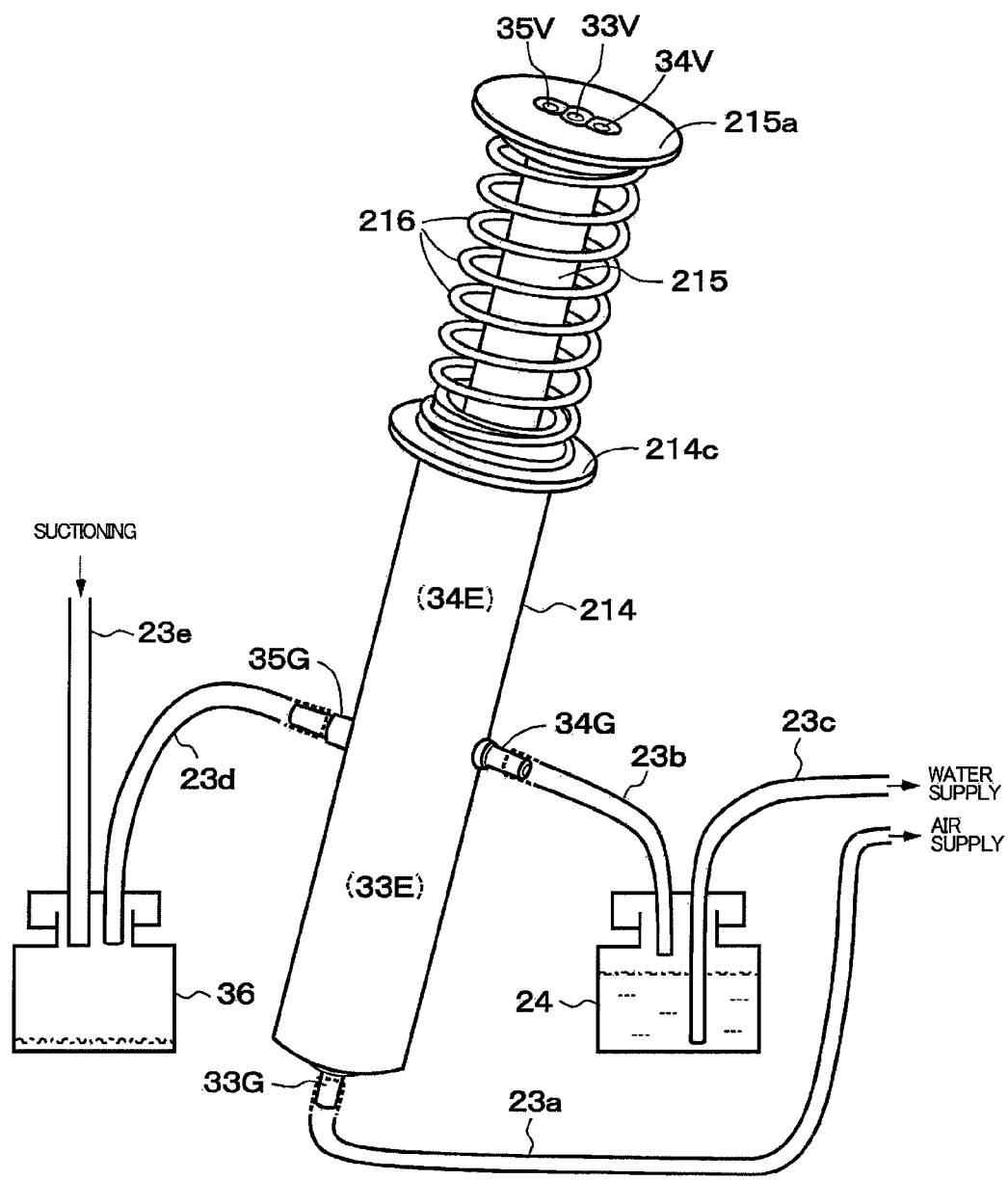
FIG. 9 is a diagram illustrating a configuration when the syringe of the third embodiment is applied to an endoscope.
Figure 10:
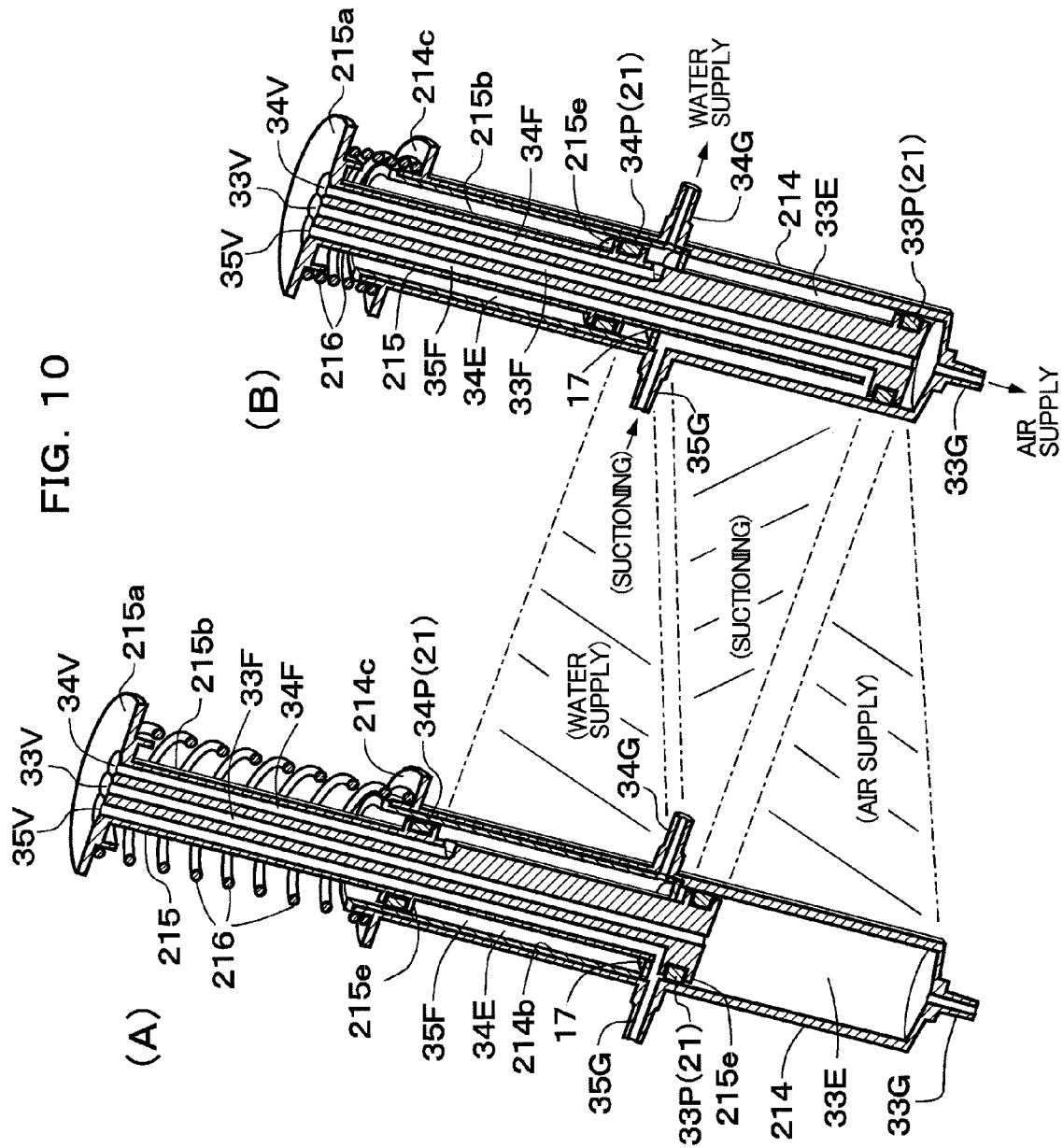
FIG. 10 show an operation of the syringe of the third embodiment, in which (A) is a sectional view when the syringe is not operated, while (B) is a sectional view in the pushing operation.

FIG. 9 shows a configuration in which the syringe of the third embodiment is applied to an endoscope device, and in this case, an air supply tube of the endoscope is connected to the first syringe port 33G of the cylindrical body 214 (first chamber 33E) through the connection tube 23a, the water supply tank 24 is connected to the second syringe pot 34G (second chamber 34E) through the connection tube 23b, and a water supply tube of the endoscope is connected to the water supply tank 24 through the connection tube 23c. Also, a suction tank 36 is connected to the suction port 35G through a connection tube 23d, and the suction tank 36 is connected to a suction tube of the endoscope through the connection tube 23e.

According to the syringe of the third embodiment as above, by pressing the pusher portion 215a while closing the first ventilation hole 33V from the basic state (non-operated state) in FIG. 10A, air in the first chamber 33E is pushed out through the first syringe port 33G so that air can be supplied, while by pressing the pusher portion 215a while closing the second ventilation hole 34V, the air in the second chamber 34E is pushed out through the second syringe port 34G so that air can be supplied. Also, by pressing the pusher portion 215a while closing the third ventilation hole 35V, the air flows into the third chamber 34E through the suction port 35G so that suctioning can be performed while air is discharged through the first ventilation path 33F and the first ventilation hole 33V.

On the other hand, if the pressing operation on the pusher portion 215a is released from the state in FIG. 10B, with regard to the air supply, since the first ventilation hole 33V and the second ventilation hole 34V are opened, and the piston body 215 is urged by the spring 216 to the rear side, the outside air is supplied into the first chamber 33E and the second chamber 34E from the first ventilation hole 33V and the second ventilation hole 34V through the first ventilation path 33F and the second ventilation path 34F so that the piston body 215 is automatically returned to the original state in FIG. 10A. If the third ventilation hole 35V relating to the suctioning is opened, the air having flown into the first chamber 33E is discharged to the outside through the third ventilation path 35F and the third ventilation hole 35V so that the piston body 215 is returned to the original position. In this way, by performing the operation on the pusher portion 215*a* repeatedly, the air supply and suctioning without limitation on the supply amount can be performed.

As shown in FIG. 9, if the third embodiment is applied to the endoscope device, by pressing the pusher portion 215*a* while closing the first ventilation hole 33V, for example, air is supplied to the observation window from the first syringe port 33G through the air supply tube of the endoscope, while by pressing the pusher portion 215*a* while closing the second ventilation hole 34V, water is supplied to the observation window through the water supply tube of the endoscope via the water supply tank 24 by means of air supply from the second syringe port 34G. Moreover, by pressing the pusher portion 215*a* while closing the third ventilation hole 35V, a fluid or the like in an observed body is sucked through the suction tank 36 from the suction port 35G and a suction tube of the endoscope (and a treatment instrument insertion channel), and the fluid or the like is reserved in the suction tank 36. In these actions, by operating the pusher portion 215*a* continuously, air/water supply or suctioning can be performed without limitation on the supply amount through the selected syringe ports 33G to 35G.

Fourth Embodiment

Figure 11:
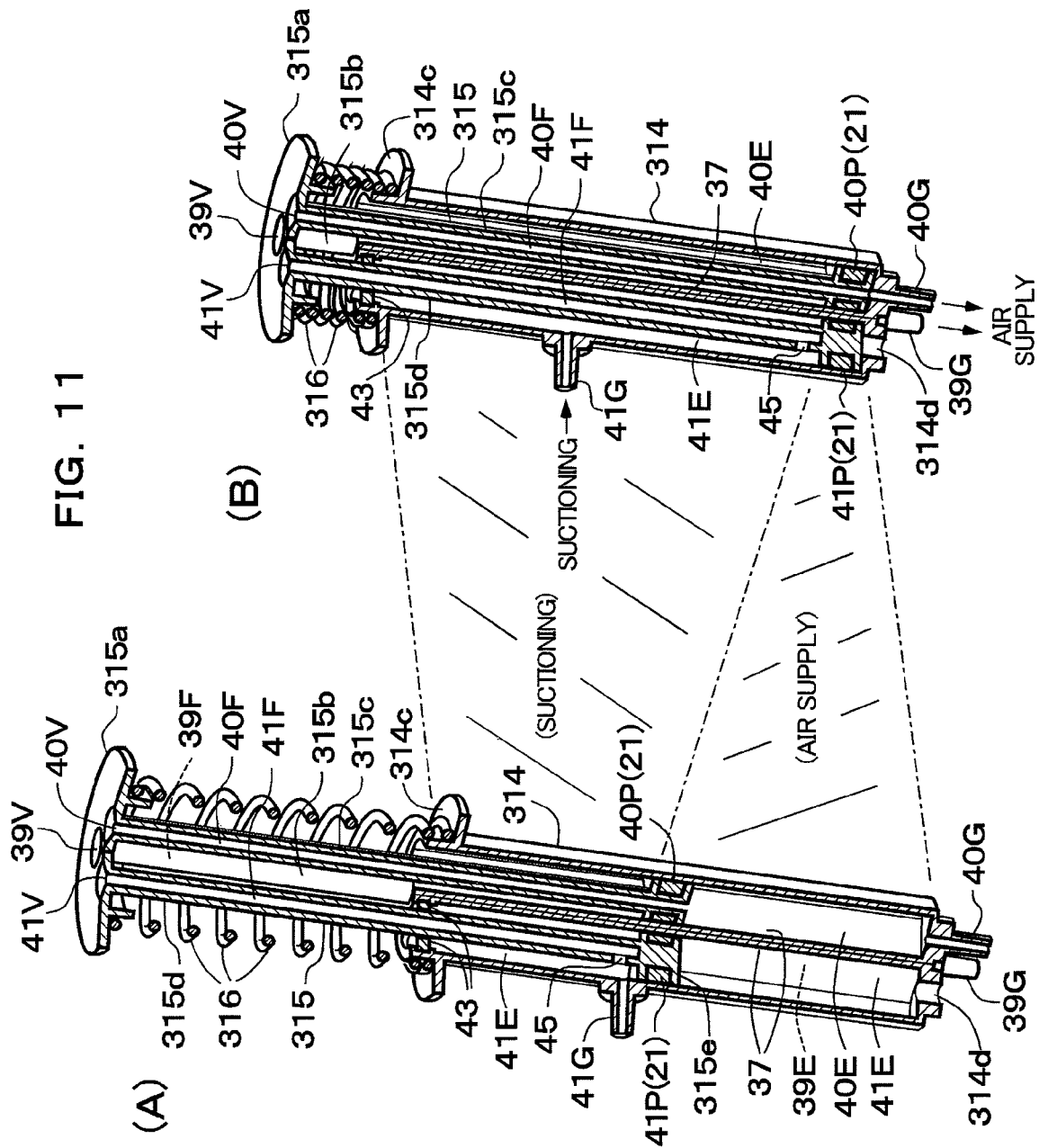
FIG. 11 show a configuration of an automatic return syringe of a fourth embodiment, in which FIG. (A) is a sectional view when the syringe is not operated, while (B) is a sectional view in the pushing operation.
Figure 12:
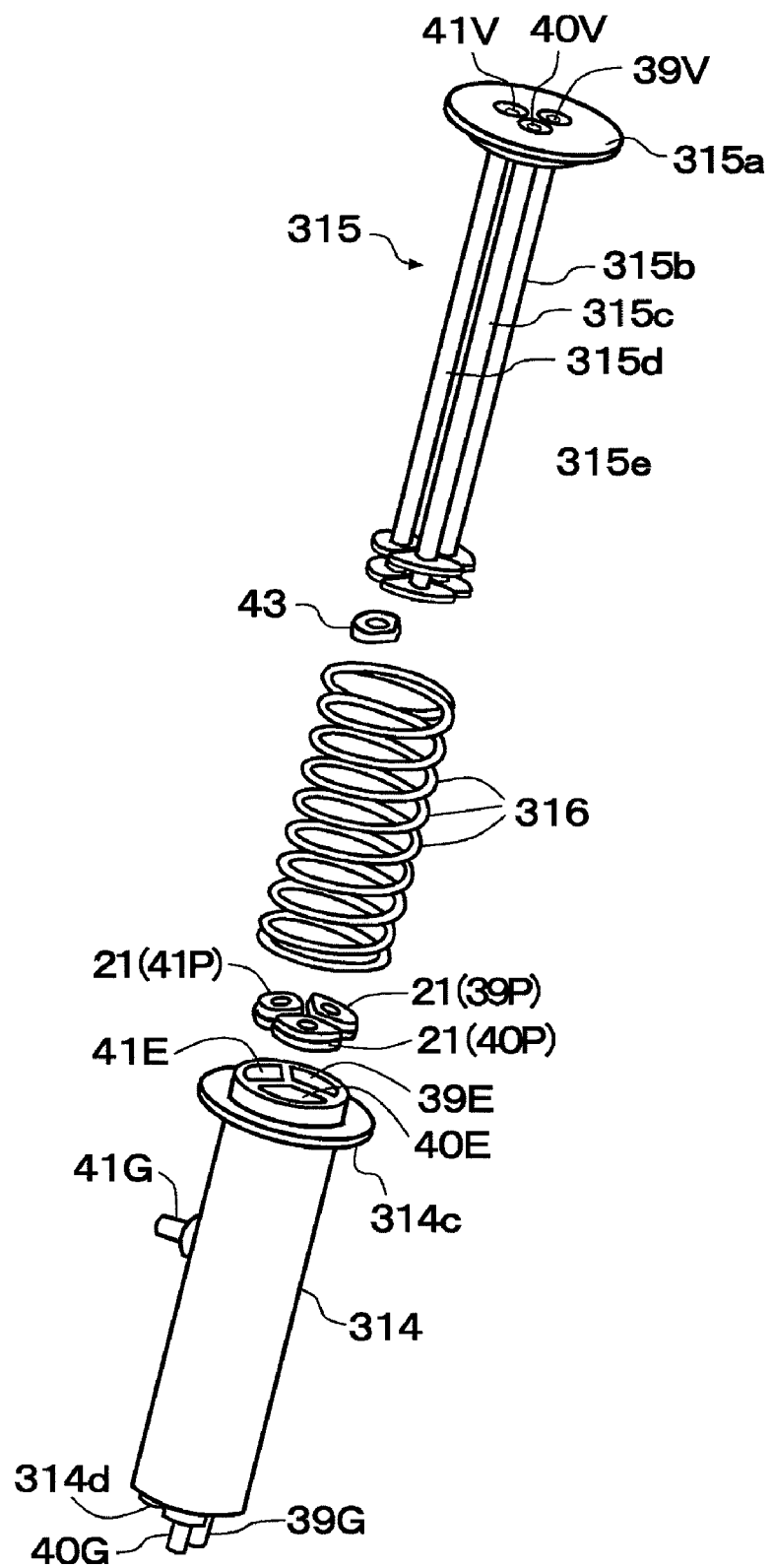
FIG. 12 is an exploded perspective view illustrating a configuration of the syringe of the fourth embodiment.
Figure 13:
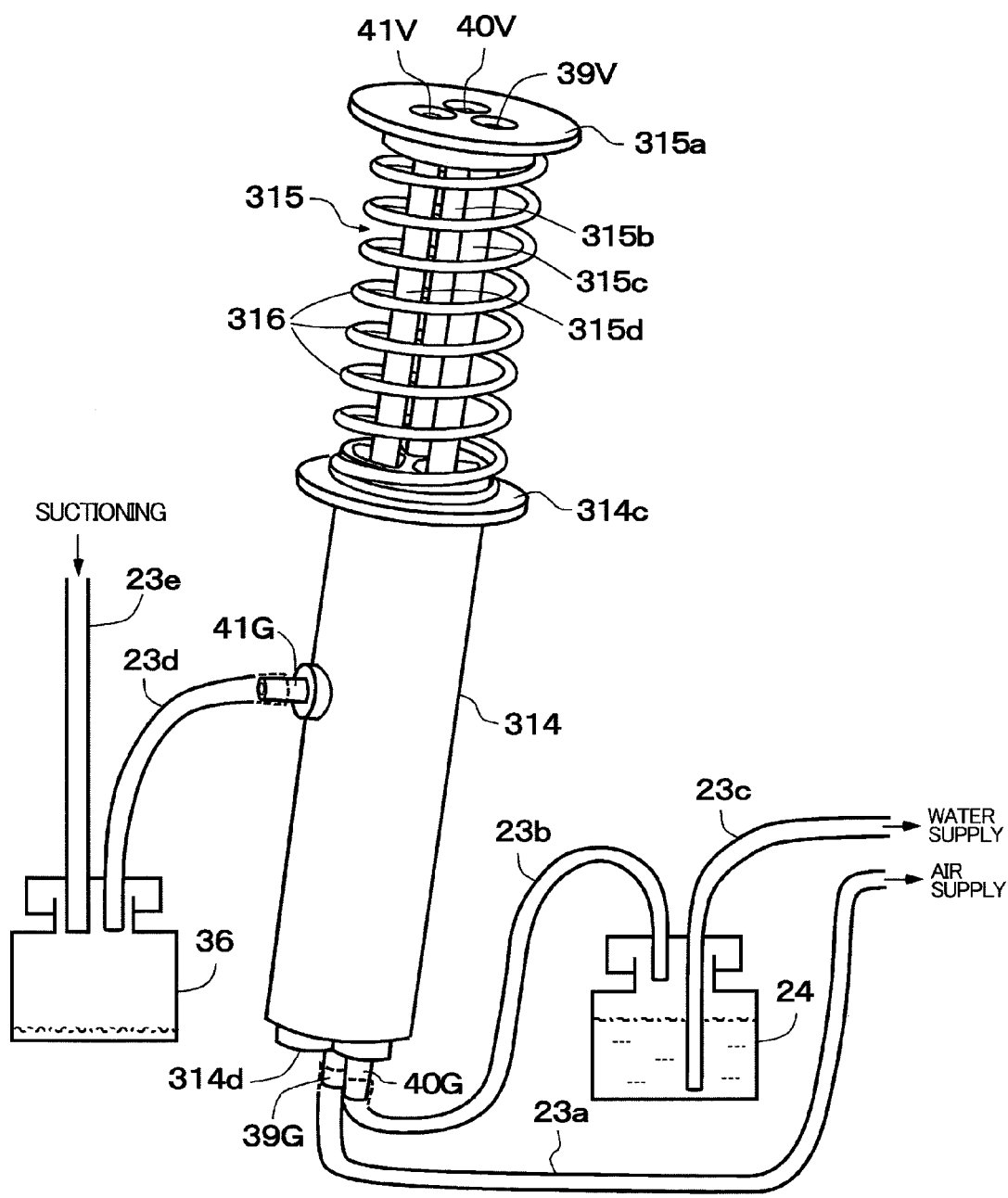
FIG. 13 is a diagram illustrating a configuration when the syringe of the fourth embodiment is applied to an endoscope.

FIGS. 11 to 13 show a configuration of a fourth embodiment, and the fourth embodiment has a configuration in which two syringe space portions are arranged in parallel similarly to the second embodiment so that suction can be also performed. The syringe in the fourth embodiment also comprises a cylindrically-shaped cylindrical body 314, a piston body 315 and a spring 316, and in the cylindrical body 314, a first chamber 39E (a portion hidden in the depth of the figure), a second chamber 40E, and a third chamber 41E as syringe space portions through which a piston portion reciprocally moves are formed in parallel inside by arranging a partition plate 37 so as to divide the columnar space longitudinally into three parts as shown in the figure.

The third chamber 41E is made as a closed space portion for suctioning by closing an upper part of the cylindrical body 314 with a partition plate 43, and a ventilation port 314*d* is formed at a distal end side of the third chamber 41E. A first syringe port 39G is provided at a distal end of the first chamber 39E (cylindrical body 314), a second syringe port 40G is provided at a distal end of the second chamber 40E, and a suction port 41G is provided in an intermediate portion of the third chamber 41E and at a position on the rear side from the reference (non-operated) position of the piston portion (41P), which will be described later.

On the other hand, the piston body 315 is provided with a disc-shaped pusher portion 315*a* at its rear end, three columnar-rod shaped shaft portions 315*b*, 315*c*, 315*d*, and a first piston portion 39P, a second piston portion 40P, and a third piston portion 41P sliding in close contact with an inner face of each of the chambers 39E to 41E are provided at distal ends of the shaft portions 315*b*, 315*c*, 315*d*. These first to third piston portions 39P to 41P are formed by mounting an annular rubber member 21 for close contact with inner face of each chamber on a fitting portion (annular groove portion, for example) 315*e* of the columnar-rod shaped shaft portions 315*b*, 315*c*, 315*d*.

Also, in the piston body 315, a first ventilation hole 39V, a second ventilation hole 40V, and a third ventilation port 41V are formed in the pusher portion 315*a*, a first ventilation path 39F penetrating from the first ventilation hole 39V to the distal end of the shaft portion in the axial direction is formed in the shaft portion 315*b*, a second ventilation path 40F penetrating from the second ventilation hole 40V to the distal end of the shaft portion is formed in the shaft portion 315*c*, and a third ventilation path 41F penetrating from the third ventilation hole 41V to a ventilation port 45 formed on a side face of the upper part of the piston portion 41P is formed in the shaft portion 315*d*. Moreover, the spring 316 urging the piston body 315 having advanced to the direction to return to the original position is provided between a flange portion 314*c* on the rear side of the cylindrical body 314 and the pusher portion 315*a*.

FIG. 13 shows a configuration when the syringe of the fourth embodiment is applied to an endoscope device, and in this case, an air supply tube of the endoscope is connected to the first syringe port 39G of the cylindrical body 314 (first chamber 39E) through the connection tube 23*a*, a water supply tank 24 is mounted on the second syringe port 40G (second chamber 40E) through the connection tube 23*b*, and a water supply tube of the endoscope is connected to the water supply tank 24 through the connection tube 23*c*. Also, the suction tank 36 is connected to the suction port 41G through the connection tube 23*d*, and this suction tank 36 is connected to a suction tube of the endoscope through the connection tube 23*e*.

According to the syringe of the fourth embodiment as above, by pressing the pusher portion 315*a* while closing the first ventilation hole 39V from the basic state (non-operated state) in FIG. 11A, air in the first chamber 39E is pushed out through the first syringe port 39G so as to perform air supply, or by pressing the pusher portion 315*a* while closing the second ventilation hole 40V, air in the second chamber 40E is pushed out through the second syringe port 40G so as to perform air supply. Also, by pressing the pusher portion 315*a* while closing the third ventilation hole 41V, air flows into the third chamber 41E through the suction port 41G, while air is discharged from the ventilation port 314*d* so that suctioning can be performed.

On the other hand, by releasing the pressing operation on the pusher portion 315*a* from the state in FIG. 11B, with regard to the air supply, the first ventilation hole 39V and the second ventilation hole 40V are opened, and the piston body 315 is urged by the spring 316 to the rear side. Thus, the outside air is supplied from the first ventilation hole 39V and the second ventilation hole 40V into the first chamber 39E and the second chamber 40E through the first ventilation path 39F and the second ventilation path 40F, and the piston body 315 is automatically returned to the original position in FIG. 11A. Also, if the third ventilation hole 41V relating to suctioning is opened, the air having flown into the third chamber 41E is discharged to the outside from the ventilation port 45 through the third ventilation path 41F and the third ventilation hole 41V, and the piston body 315 is returned to the original position. In this way, by operating the pusher portion 315*a* repeatedly, the air supply and suctioning without limitation on the supply amount can be performed from the selected syringe ports 39G to 42G.

If the fourth embodiment is applied to an endoscope device as shown in FIG. 13, by pressing the pusher portion 315*a* while closing the first ventilation hole 39V, for example, air is supplied to the observation window from the first syringe port 39G through an air supply tube of the endoscope, or by pressing the pusher portion 315*a* while closing the second ventilation hole 40V, by means of air supply from the second syringe port 40G, water is supplied to the observation window through a water supply tube of the endoscope via the water supply tank 24, and moreover, by pressing the pusher portion 315a while closing the third ventilation hole 41V, suctioning of a fluid or the like in an observed body is performed from the suction port 41G through the suction tank 36 and a suction tube of the endoscope (and a treatment instrument insertion channel), and the liquid or the like is reserved in the suction tank 36.

In the above embodiment, the example is shown in which two syringe space portions relating to the air supply and a single syringe space portion relating to the suctioning are provided, but three syringe space portions relating to the air supply may be provided or two syringe portions relating to the suctioning may be provided. Also, in the description on each of the above embodiment, the case in which the respective ventilation holes 19V to 41V are closed one by one in operation was explained, but it is possible to perform the operation by closing two or more holes at the same time.

Fifth Embodiment

Figure 14:
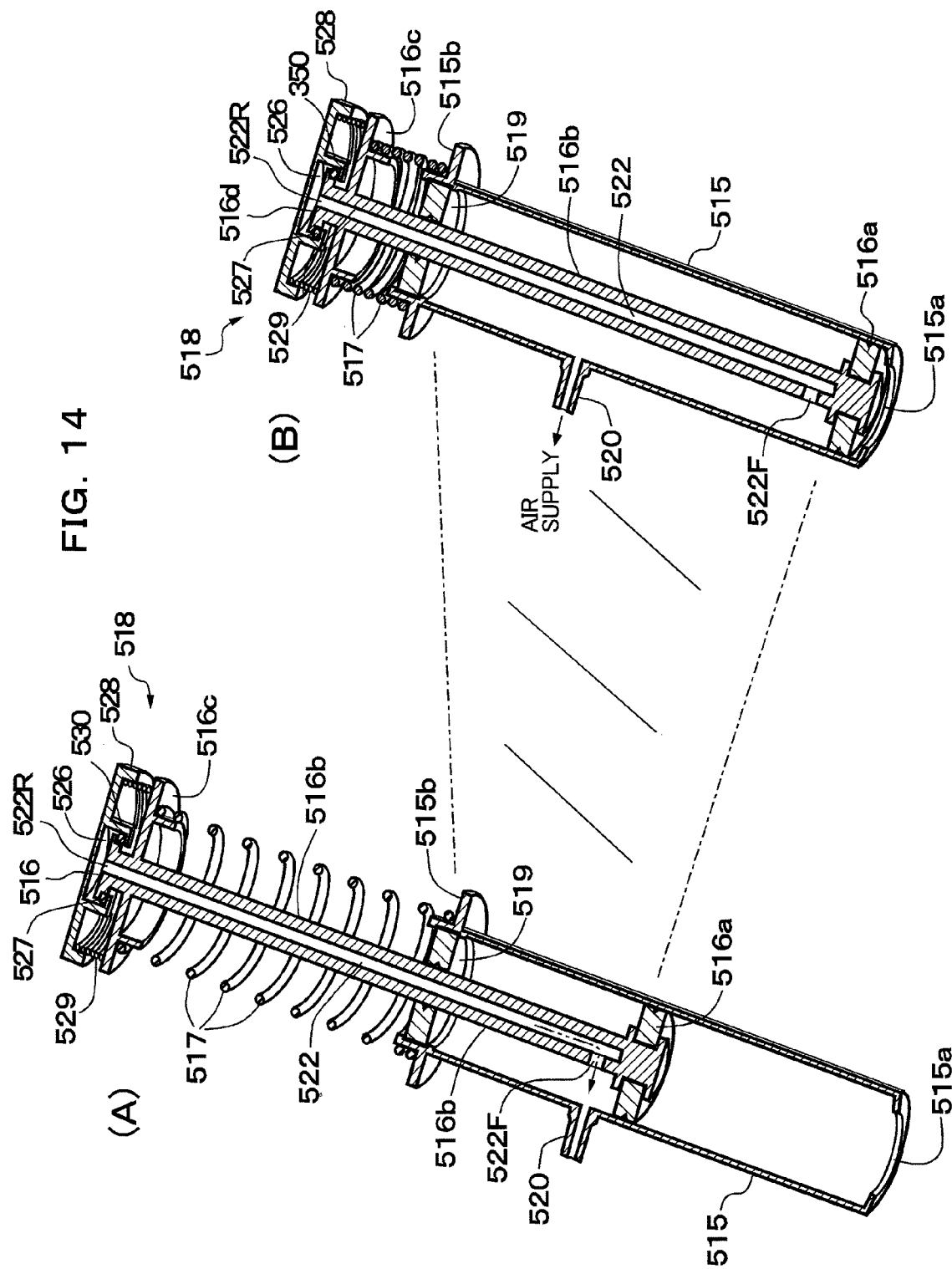
FIG. 14 show a configuration of an automatic return syringe of a fifth embodiment of the present invention, in which (A) is a sectional view when the syringe is not operated, while (B) is a sectional view in the pushing operation.
Figure 15:
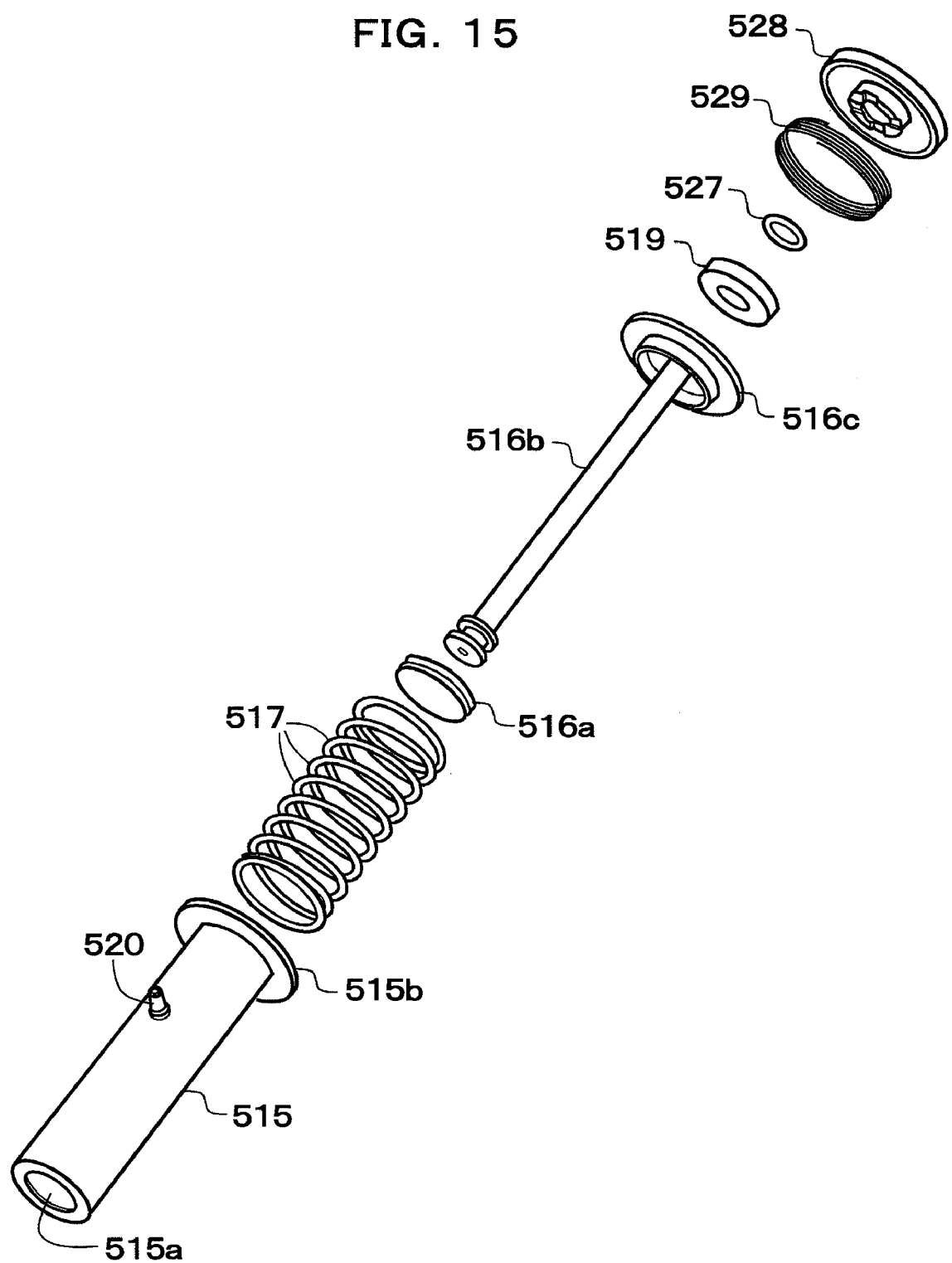
FIG. 15 is an exploded perspective view illustrating a configuration of the automatic return syringe of the fifth embodiment.
Figure 16:
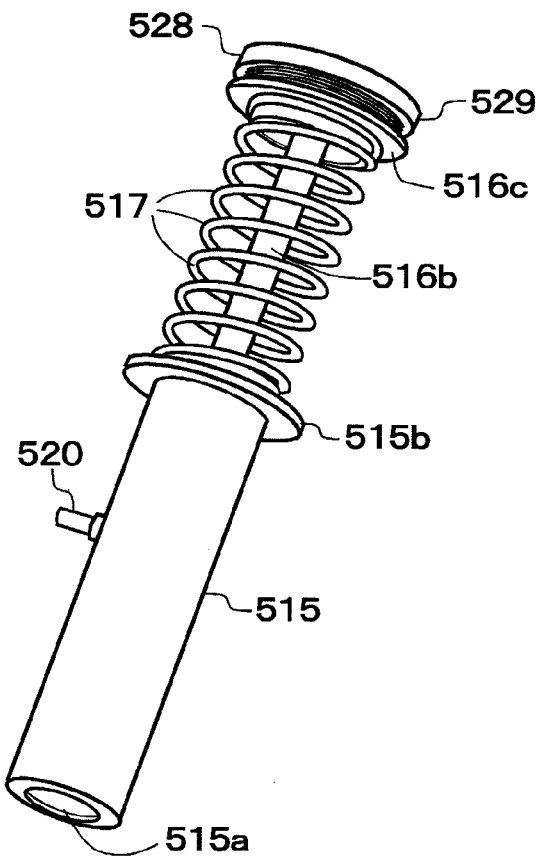
FIG. 16 is a perspective view of the automatic return syringe of the firth embodiment.
Figure 19:
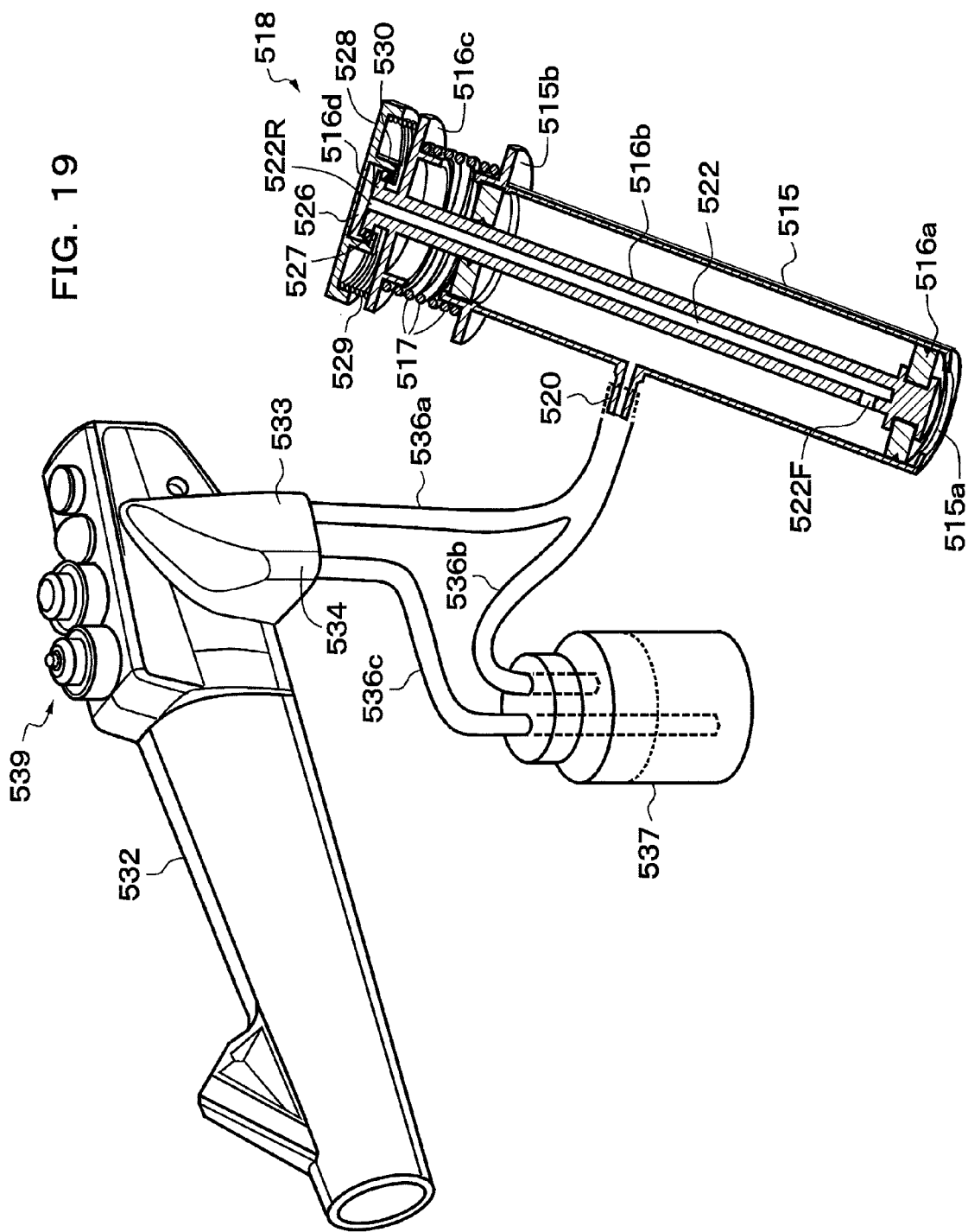
FIG. 19 is a perspective (partially sectional) view illustrating a configuration of an endoscope device using the automatic return syringe according to the fifth embodiment, showing a state in the pushing operation.
Figure 20:
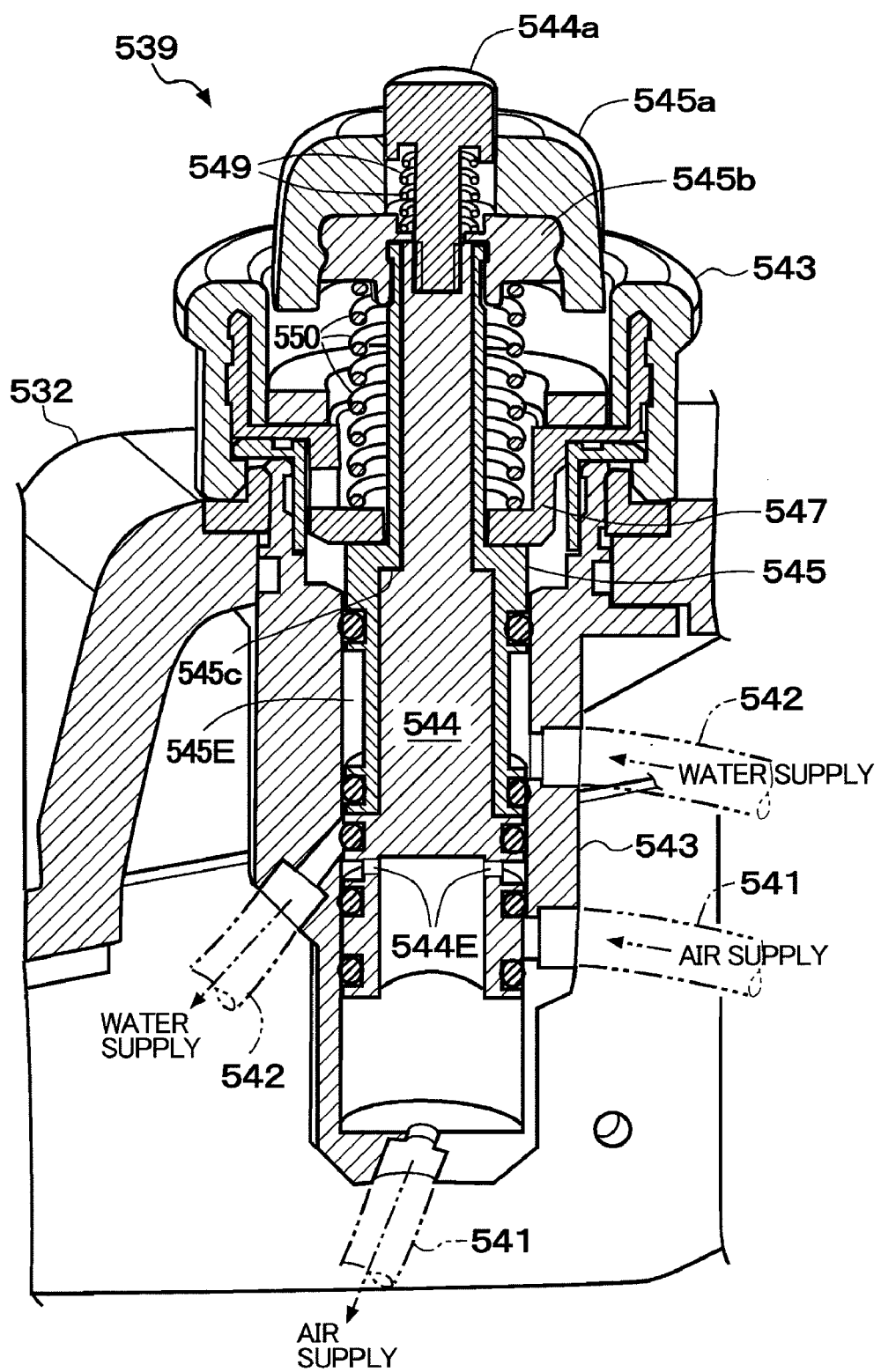
FIG. 20 is a sectional view illustrating a configuration of an air/water supply operation portion of the endoscope device according to the fifth embodiment.

FIGS. 14 to 18 show a configuration of an automatic return syringe according to a fifth embodiment, and FIGS. 19 to 21 show a configuration of a case in which the automatic return syringe in FIG. 14 is applied to an endoscope device. In FIG. 14, the syringe of the firth embodiment comprises a cylindrically-shaped cylindrical body 515, a piston body (slider) 516, a first spring (spring) 517, and a pushing operation portion 518. In the cylindrical body 515, an opening (ventilation port) 515a is formed at its distal end face, a rear end portion is closed by a partition plate 519 made of a rubber member, for example, and a syringe port 520 is provided on a side face.

On the other hand, the piston body 516 is provided with a disc-shaped piston portion (sliding portion made of a rubber member, for example) 516a sliding (reciprocally moving) in close contact with an inner face of the cylindrical body 515 and having a predetermined thickness and a columnar-rod state shaft portion 516b supporting the piston portion 516a, and a first ventilation path (conduit) 522 is provided at a center part in the radial direction of this shaft portion 516b, the first ventilation path 522 being formed from a shaft-portion rear end port 522R to a side face port 522F on the shaft-portion distal-end side. The piston portion 516a is formed by fitting/arranging a central through hole of the disc-shaped rubber member in an annular groove portion on the outer circumference of the shaft portion 516b.

Figure 17A:
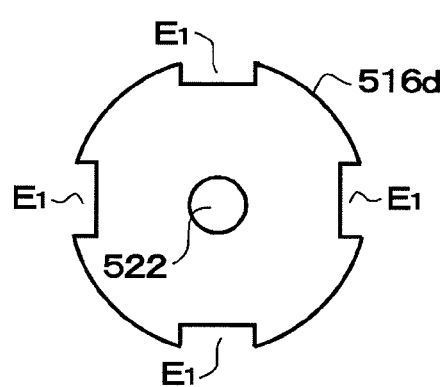
Figure 17B:
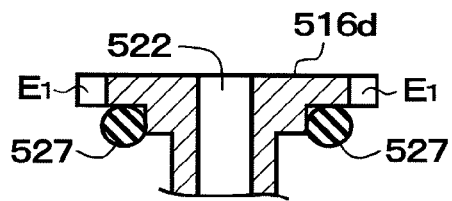

The pushing operation portion 518 is integrally provided at the rear end portion of the shaft portion 516b, and as shown in enlarged diagrams of FIGS. 18A and 18B, the pushing operation portion 518 comprises a supporting disc portion 516c on the piston body 516 side, a small disc portion 516d for forming a second ventilation path 526, an O-ring 527, a circular crown-like pushing body 528, and a second spring (spring) 529. That is, the small disc portion 516d has the O-ring 527 mounted on a stepped portion formed on the lower side (distal end side), and as shown in FIGS. 17A and 17B, a ventilation groove $E_1$ for constituting a part of the second ventilation path 526 is cut in and formed at plural locations (four locations, for example) on the outer circumference of the small disc portion 516d.

Figure 17C:
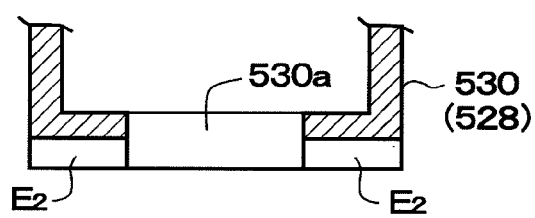
Figure 17D:
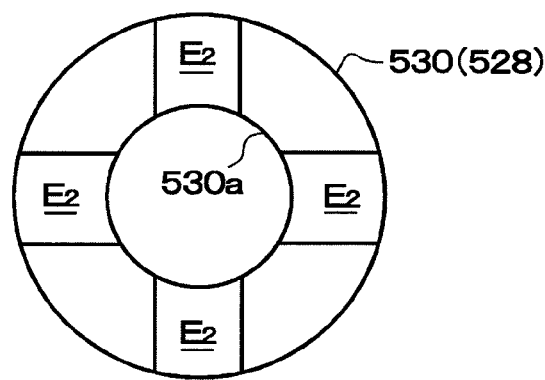

On the crown-like pushing body 528, a surrounding body 530, which is a circular dish-like body forming a circular cavity with a radius slightly smaller than a radius of the small disc portion 516d and has a circular opening 530a opened at its center position of the lower side (distal end side) thereof, is provided, and the small disc portion 516d is arranged in the surrounding body 530. In the surrounding body 530, as shown in FIGS. 17C and 17D, a ventilation groove $E_2$ formed from the circular opening 530a toward the outer circumferential side is provided at plural locations (four locations, for example) in the circumferential direction of its bottom face portion (distal end side). Then, the second spring 529 is arranged between the crown-like pushing body 528 and the supporting disc portion 516c so as to urge the pushing body 528 in the direction of the rear end.

According to the pushing operation portion 518 as above, as shown in FIG. 18A, when the operation of the pushing body 528 is released, the pushing body 528 is moved by means of urging of the second spring 529 to the rear end side, and since the inner face of the surrounding body 530 (inner face of the dish-shaped bottom face portion) is brought into close contact with the O-ring 527 below the small disc portion 516d, the second ventilation path 526 is brought into a closed state. On the other hand, as shown in FIG. 18B, in the pushing operation of the pushing body 528, the pushing body 528 is moved to the piston body side on the distal end side and the inner face of the surrounding body 530 is separated from the O-ring 527, and the second ventilation path 526 communicating with the first ventilation path 522 is brought into an open state. That is, the second ventilation path 526 is made up of a space in the surrounding body 530 communicating with the first ventilation path 522, the ventilation groove $E_1$, the circular opening 530a, and the ventilation groove $E_2$, and the outside air is introduced through the ventilation groove $E_2$.

Moreover, the first spring 517 is arranged between a flange portion 515b on the rear side of the cylindrical body 515 and the supporting disc portion 516c of the pushing operation portion 518 (in a state engaging with each other) and is capable of returning (reversing) the piston body 516 having been pushed to the original position.

According to the automatic return syringe as above, by pressing the pushing body 528 (pushing operation portion 518) with the thumb or the like against an urging force of the second spring 529 from the basic state (non-operated state) in FIG. 14A (first-stage pressing), as also shown in FIG. 18B, the pushing body 528 is moved to the piston body side, the inner face of the surrounding body 530 is separated from the O-ring 527, and the second ventilation path 526 constituted by the inner space of the surrounding body 530, the ventilation groove $E_1$, the circular opening 530a, and the ventilation groove $E_2$ is brought into an open state. Then, by pressing the pushing body 528 against the urging force of the first spring 517 (second-stage pressing), the outside air flows into the cylindrical body 515 through the second ventilation path 526 and the first ventilation path 522 (rear-end port 522R, side face port 522F on the distal end side) and the air in the front of the piston portion 516a in the cylindrical body 515 flows out of the opening 515a so that the piston body 516 can be advanced to the distal-end side position without sucking air through the syringe port 520 and brought into the state in FIG. 14B.

If the operation on the pushing body 528 is released in the state of FIG. 14B, as also shown in FIG. 18A, the inner face of the surrounding body 530 is brought into close contact with the O-ring 527, the second ventilation path 526 is brought into a closed state, the outside air no longer flows into the cylindrical body 515 through the first ventilation path 522, the piston body 516 is returned by the first spring 517, and the air in the cylindrical body 515 is fed through the syringe port 520. Therefore, by connecting the syringe port 520 to a destination portion by a tube or the like, air can be supplied to the destination portion, and by connecting it to a water supply portion, water can be also supplied through the water supply portion. The two-stage pressing operation by the pusher body 528 can be performed repeatedly after air supply, and air supply without limitation on an amount can be performed by continuous plural times of operations.

FIG. 19 is a configuration in which the automatic return syringe is applied to an endoscope device as an air/water supply device, and as shown in the figure, in an endoscope operation portion 532, an air supply port (air supply tube connection port) 533 and a water supply port (water supply tube connection port) 534 are provided. The syringe port 520 of the automatic return syringe is connected to the air supply port 533 through a connection tube 536a, which is one of a bifurcated (branched) tube, a connection tube 536b, which is the other of the bifurcated tube, is connected and arranged to a water supply tank 537 (one of connection ports), and the water supply tank 537 (the other of the connection ports) is connected to the water supply port 534 through the connection tube 536c. Also, an air/water supply operation portion 539 is provided in this endoscope operation portion 532.

FIG. 20 shows an internal configuration of the air/water supply operation portion 539, and the air/water supply operation portion (air supply tube and water supply tube opening/closing mechanism) 539 comprises a cylindrical receiving portion 543 in which an air supply tube 541 and a water supply tube 542 are disposed, a first shaft body (piston) 544 arranged vertically movably in the receiving portion 543, and a second shaft body 545 arranged on the outer circumference side of the first shaft body 544 and regulating movement to the upper side of the first shaft body 544 with a stepped portion 545c having an inner diameter made small. In the first shaft body 544, a connection path (hole penetrating in the shaft body) 544E communicating with the air supply tube 541 when being pressed down is formed, and a first-stage pushing portion (air supply pushing portion) 544a is provided at the upper part, a connection path (portion whose outer circumferential diameter is made small) 545E communicating with the water supply tube 542 when being pressed down is formed in the second shaft body 545, and a second-stage pushing portion (water supply pushing portion) 545a is provided through a connection member 545b at the upper part. The first-stage pushing portion 544a is arranged vertically movably in the central through hole of the second-stage pushing portion 545a.

The second shaft body 545 has its upward movement regulated by a supporting plate 547 on the receiving portion 543 side, while the first shaft body 544 has its upward movement regulated by the second shaft body 545 as mentioned above. Also, a third spring (spring) 549 for urging the first shaft body 544 upward is provided between a lower face of the pushing portion 544a of the first shaft body 544 and an upper face of the connection member 545b of the pusher portion 545a, and a fourth spring 550 for urging the second shaft body 545 upward is provided between the lower face of the connection member 545b of the pushing portion 545a and the upper face of the supporting plate 547 on the receiving portion 543 side.

According to the air/water supply operation portion (air supply tube and water supply tube opening/closing mechanism) 539 as above, if the first-stage pushing portion 544a protruding to the upper part of the center part is pressed, the first shaft body 544 is moved downward singularly (advances), and by having the connection path 544E communicate with the air supply tube 541, the air supply tube 541 is opened, and moreover, if the second-stage pushing portion 545a is pressed, the second shaft body 545 is moved downward with the first shaft body 544, and by having the connection path 545E communicate with the water supply tube 542, the water supply tube 542 is opened.

According to the endoscope device as above, in the automatic return syringe, by performing the first stage pushing operation on the pusher body 528 with the thumb or the like from the basic state in FIG. 14A, as described in FIG. 18B, the pusher body 528 is moved to the piston body side, and the inner face of the surrounding body 530 is separated from the O-ring 527 so that the second ventilation path 526 constituted by the inner space of the surrounding body 530, the ventilation groove $E_1$, the circular opening 530a, the ventilation groove $E_2$ is brought into the open state. Then, by performing the second-stage pushing operation on the pusher body 528, the outside air is supplied into the cylindrical body 515 through the second ventilation path 526 and the first ventilation path 522 so that the piston body 516 is moved to the distal-end side position and stopped as in FIG. 19 and is brought into a state (air-supply power charged state) in which air supply from the syringe port 520 can be performed.

Figure 21A:
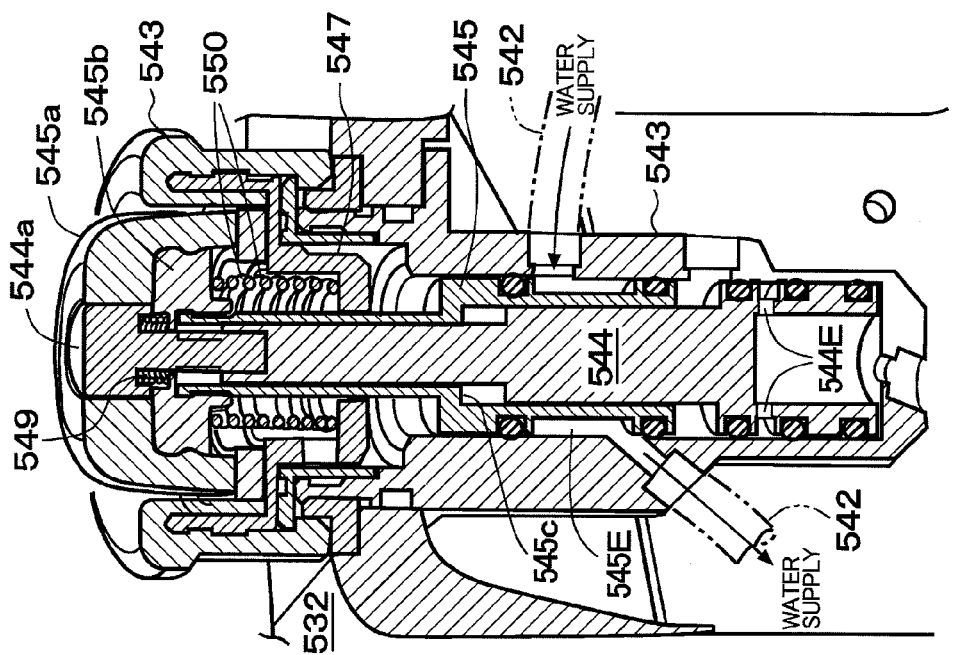
FIG. 21A is a sectional view when a first-stage pusher portion is operated in the air/water supply operation portion of the fifth embodiment.
Figure 21B:
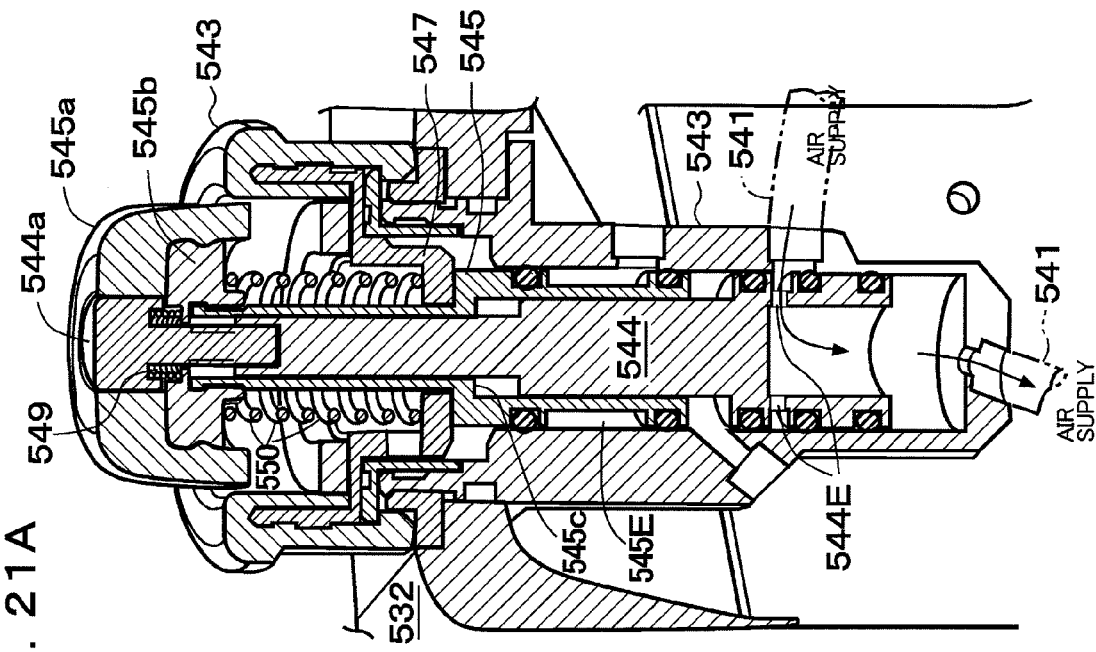
FIG. 21B is a sectional view when a second-stage pusher portion is operated.
Figure 22:
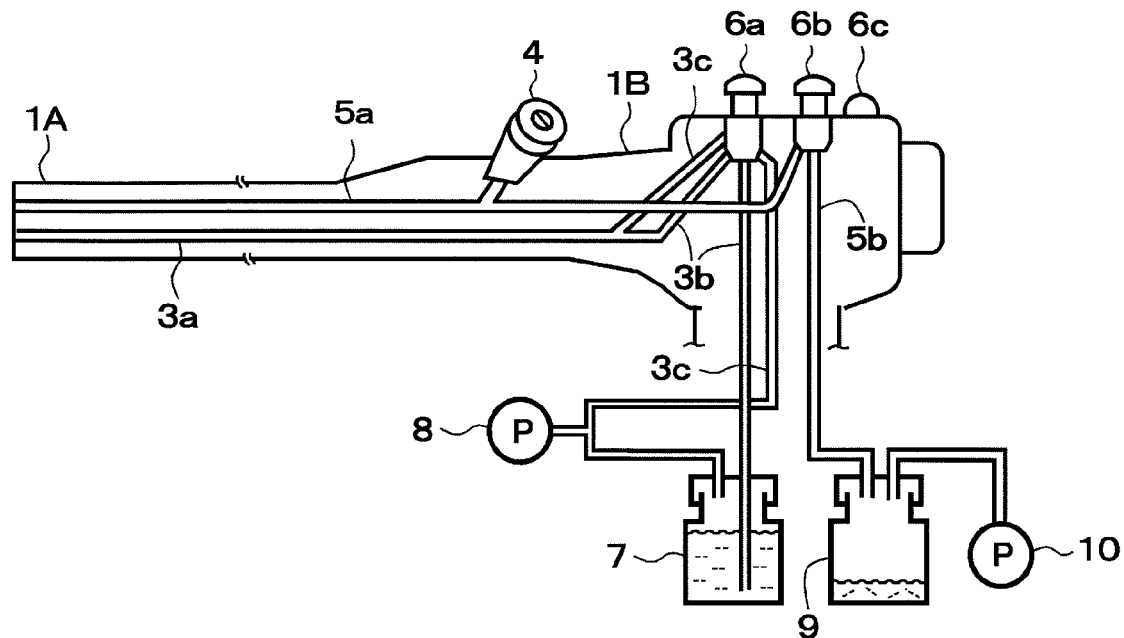
FIG. 22 is a diagram illustrating a configuration of a prior-art endoscope device.
Figure 23:
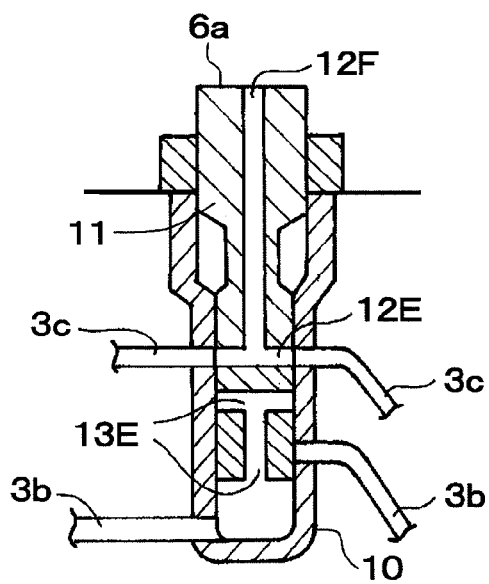
FIG. 23 is a sectional view illustrating a configuration of an air/water supply operation portion of the prior-art endoscope device.

In the air/water supply operation portion 539 in the endoscope operation portion 532, by pressing the first-stage pushing portion 544a in the state in FIG. 20, the first shaft body 544 is moved downward singularly as in FIG. 21A, and the connection path 544E is connected to the air supply tube 541 so that the air supply tube 541 is brought into the open state. Thus, air is supplied from the syringe port 520 of the automatic return syringe to the observation window through the connection tube 536a, the air supply port 533, and the air supply tube 541. Then, by pressing the second-stage pushing portion 545a, as in FIG. 21B, the second shaft body 545 is moved downward with the first shaft body 544 and the connection path 545E is connected to the water supply tube 542 so that the water supply tube 542 is brought into the open state. Thus, air is supplied into the water supply tank 537 form the syringe port 520 through the connection tube 536b, by which washing water or the like in the water supply tank 537 is supplied to the observation window through the connection tube 526c, the water supply port 534, and the water supply tube 542.

According to the operation of the air/water supply operation portion 539 as above, there is a merit that a required small amount of air or water can be supplied appropriately and easily. Also, when the piston body 516 of the automatic return syringe has fully returned to the original position, by repeating the pushing operation on the piston body 516 by the pushing operation portion 518, air/water supply without limitation on the amount can be performed.

DESCRIPTION OF SYMBOLS 14, 114, 214, 314, 515 CYLINDRICAL BODY
14d, 45, 314d VENTILATION PORT
15, 115, 215, 315, 516 PISTON BODY
15a, 115a, 215a, 315a PUSHER PORTION
16, 116, 216, 316 SPRING
19f, 29F, 33F, 39F, 522 FIRST VENTILATION PATH
20f, 30F, 34F, 40F, 526 SECOND VENTILATION PATH
35F, 41F THIRD VENTILATION PATH
19V, 29V, 33V, 39V FIRST VENTILATION HOLE
20V, 30V, 34V, 40V SECOND VENTILATION HOLE
35V, 41V THIRD VENTILATION HOLE
517 FIRST SPRING
528 PUSHING BODY
529 SECOND SPRING
CITATION LIST
Patent Document 1: JP-A-2003-135391

What is claimed is:

1. An automatic return syringe comprising:
   a cylindrical body in which a plurality of space portions divided by a partition portion are formed and a syringe port is provided in each of the plurality of space portions;
   a piston body, which is a piston reciprocally moving in the plurality of space portions in the cylindrical body and has a pusher portion at a rear end, having a plurality of ventilation paths formed through which each of the plurality of space portions communicates with each of a plurality of ventilation holes provided in the pusher portion; and a spring arranged between the piston body and the cylindrical body, for returning the piston body subjected to a pushing operation to an original position the plurality of space portions are arranged in series by laterally dividing the inside of the cylindrical body and the syringe port is provided on a side face of the cylindrical body in the space portion other than the distal-end space portion; and the piston body is provided with a piston portion reciprocally moving in close contact with an inner circumference of the plurality of space portions in the cylindrical body and a shaft portion supporting the piston portion and having an outer diameter smaller than an inner diameter of the cylindrical body, wherein an air supply or suctioning is performed independently from each syringe port.

2. The automatic return syringe according to claim 1, wherein
the plurality of space portions are arranged in parallel by longitudinally dividing the inside of the cylindrical body and the syringe port is provided at the distal end side of the cylindrical body.

3. The automatic return syringe according to claim 2, wherein
the syringe ports for air supply are arranged at distal end sides of the plurality of space portions arranged in parallel in the cylindrical body and a suction port is provided on a side face of the cylindrical body on the rear side from a position where the piston portion arranged in the plurality of space portions is not operated so that both air supply and suctioning can be performed.

4. The automatic return syringe according to claim 1, wherein
the syringe ports for air supply are arranged at distal end sides of the plurality of space portions arranged in series in the cylindrical body and a suction port is provided on a side face of the cylindrical body on the rear side from a position where the piston portion arranged in the plurality of space portions is not operated so that both air supply and suctioning can be performed.

* * * * *